US010932750B2

(12) United States Patent
Kanayama

(10) Patent No.: US 10,932,750 B2
(45) Date of Patent: Mar. 2, 2021

(54) MEDICAL DIAGNOSTIC APPARATUS AND MEDICAL ANALYSIS METHOD

(71) Applicant: CANON MEDICAL SYSTEMS CORPORATION, Otawara (JP)

(72) Inventor: Yuko Kanayama, Kawasaki (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 1001 days.

(21) Appl. No.: 15/448,187

(22) Filed: Mar. 2, 2017

(65) Prior Publication Data

US 2017/0258438 A1 Sep. 14, 2017

(30) Foreign Application Priority Data

Mar. 11, 2016 (JP) .............................. JP2016-047833

(51) Int. Cl.
| A61B 5/00 | (2006.01) |
| A61B 8/08 | (2006.01) |
| A61B 5/055 | (2006.01) |
| A61B 8/14 | (2006.01) |
| A61B 8/00 | (2006.01) |

(52) U.S. Cl.
CPC ............ *A61B 8/085* (2013.01); *A61B 5/055* (2013.01); *A61B 8/14* (2013.01); *A61B 8/463* (2013.01); *A61B 8/488* (2013.01); *A61B 8/5207* (2013.01); *A61B 8/485* (2013.01)

(58) Field of Classification Search
None
See application file for complete search history.

(56) References Cited

U.S. PATENT DOCUMENTS

| 6,402,694 B1 | 6/2002 | Bae et al. | |
| 2008/0319317 A1* | 12/2008 | Kamiyama | .......... A61B 8/0825 600/443 |
| 2009/0143676 A1* | 6/2009 | Matsumura | .............. A61B 8/08 600/438 |
| 2010/0241012 A1* | 9/2010 | Yin | ........................ A61B 5/055 600/485 |
| 2010/0249590 A1 | 9/2010 | Kanayama et al. | |
| 2014/0114189 A1* | 4/2014 | Kanayama | .......... G01S 7/52046 600/438 |

(Continued)

FOREIGN PATENT DOCUMENTS

| JP | 60-29137 A | 2/1985 |
| JP | 60-31740 | 2/1985 |

(Continued)

OTHER PUBLICATIONS

Office Action dated Feb. 12, 2020 in corresponding Japanese Patent Application No. 2016-047833, 4 pages.

*Primary Examiner* — Joel F Brutus
(74) *Attorney, Agent, or Firm* — Oblon, McClelland, Maier & Neustadt, L.L.P.

(57) ABSTRACT

According to one embodiment, a medical diagnostic apparatus includes processing circuitry and display circuitry. The processing circuitry estimates a position of a structure in a subject based on data obtained by scanning with respect to the subject and analyzes tissue characterization in the subject. The display circuitry displays an analysis result of the tissue characterization obtained by the processing circuitry with respect to a plurality of positions in the subject except for the estimated structure position.

16 Claims, 10 Drawing Sheets

(56) References Cited

U.S. PATENT DOCUMENTS

2015/0141821 A1* 5/2015 Yoshikawa .......... A61B 8/5207
  600/438

FOREIGN PATENT DOCUMENTS

| | | |
|---|---|---|
| JP | 62-152442 A | 7/1987 |
| JP | 63-105742 | 5/1988 |
| JP | 63-130054 | 6/1988 |
| JP | 3-188842 A | 8/1991 |
| JP | 7-51270 | 2/1995 |
| JP | 2000-354595 | 12/2000 |
| JP | 2001-238884 | 9/2001 |
| JP | 2003-61964 A | 3/2003 |
| JP | 2004-321582 A | 11/2004 |
| JP | 4373698 | 11/2009 |
| JP | 2010-233859 | 10/2010 |
| JP | 4921826 | 4/2012 |
| JP | 2013-5876 A | 1/2013 |
| JP | 2016-2208 A | 1/2016 |
| JP | 5925438 | 5/2016 |

* cited by examiner

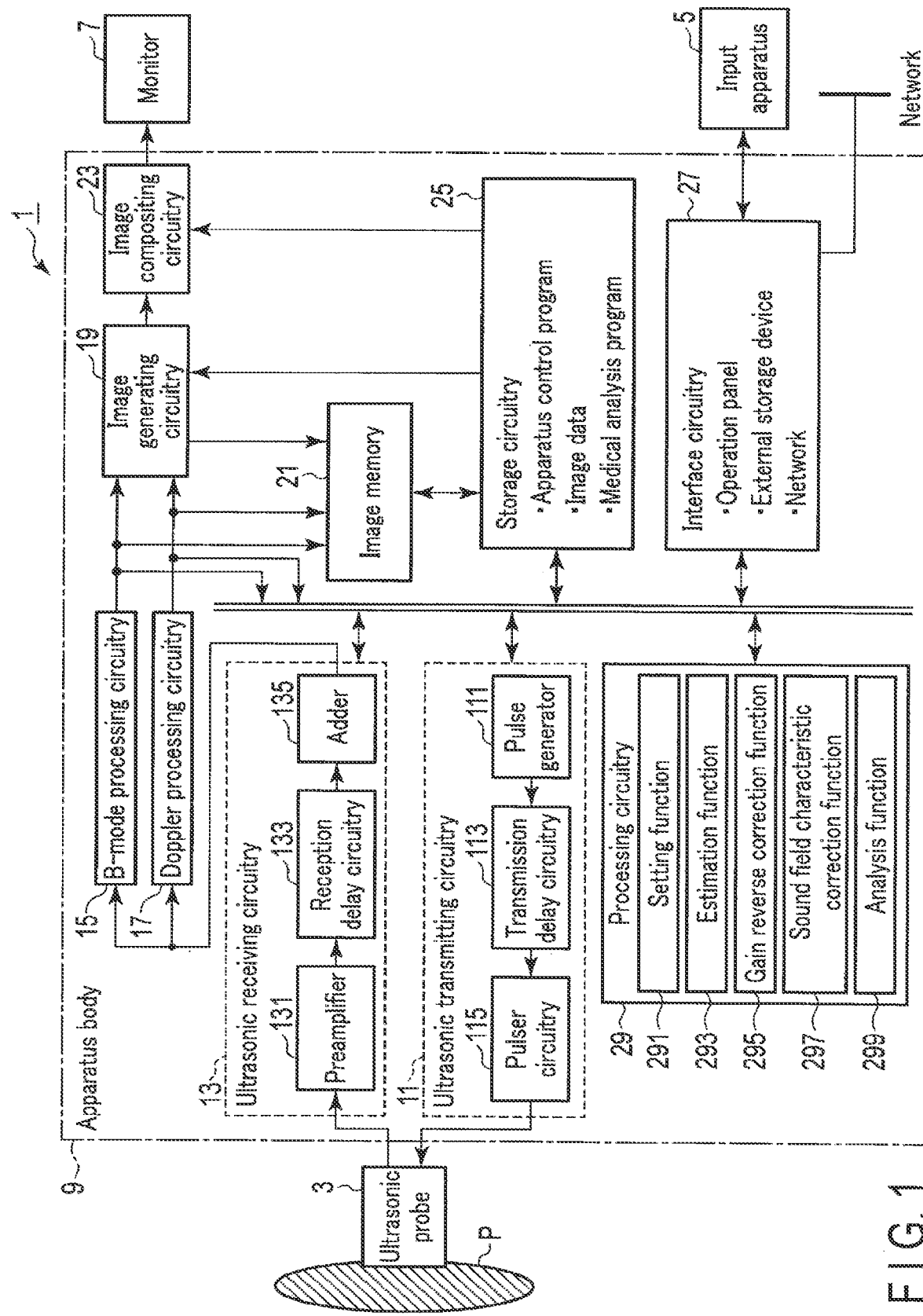
F I G. 1

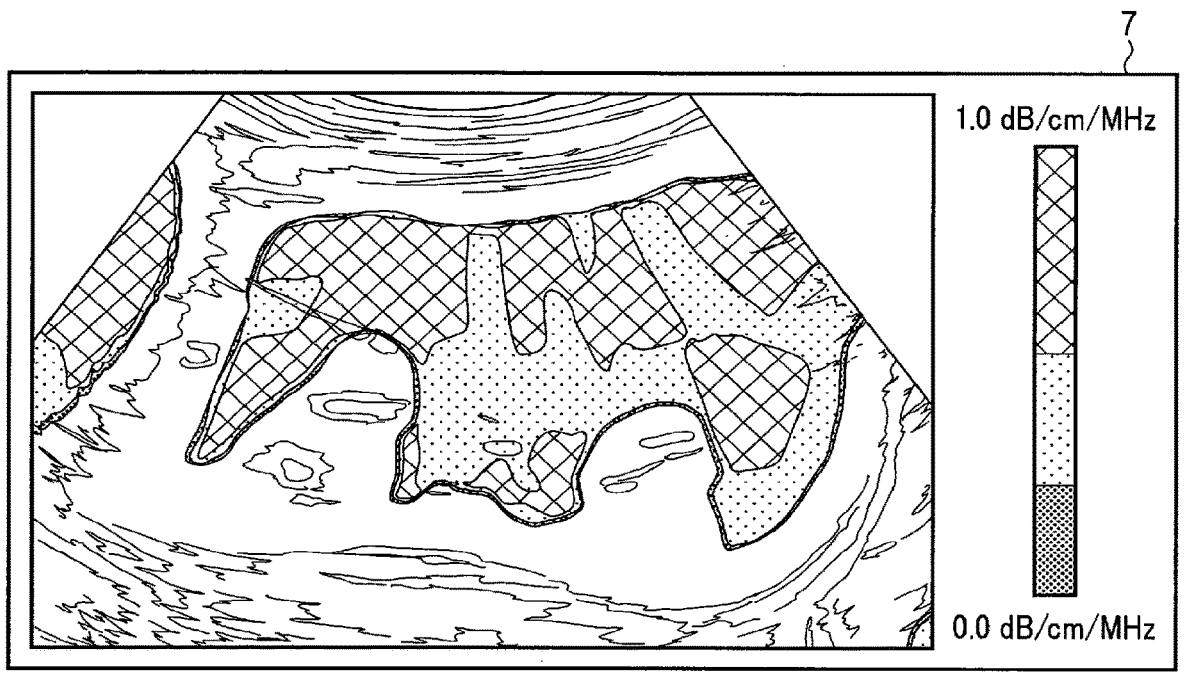
F I G. 4

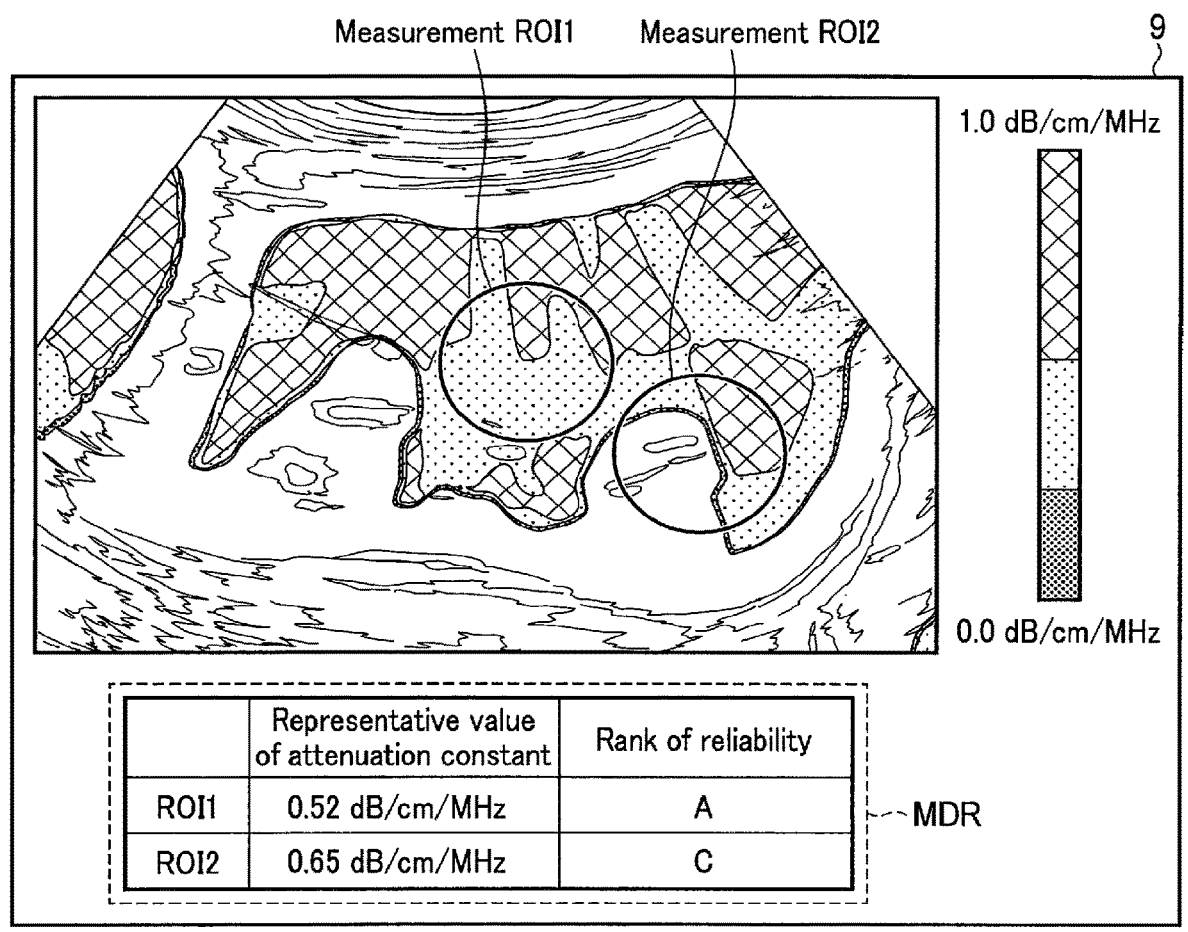
F I G. 9

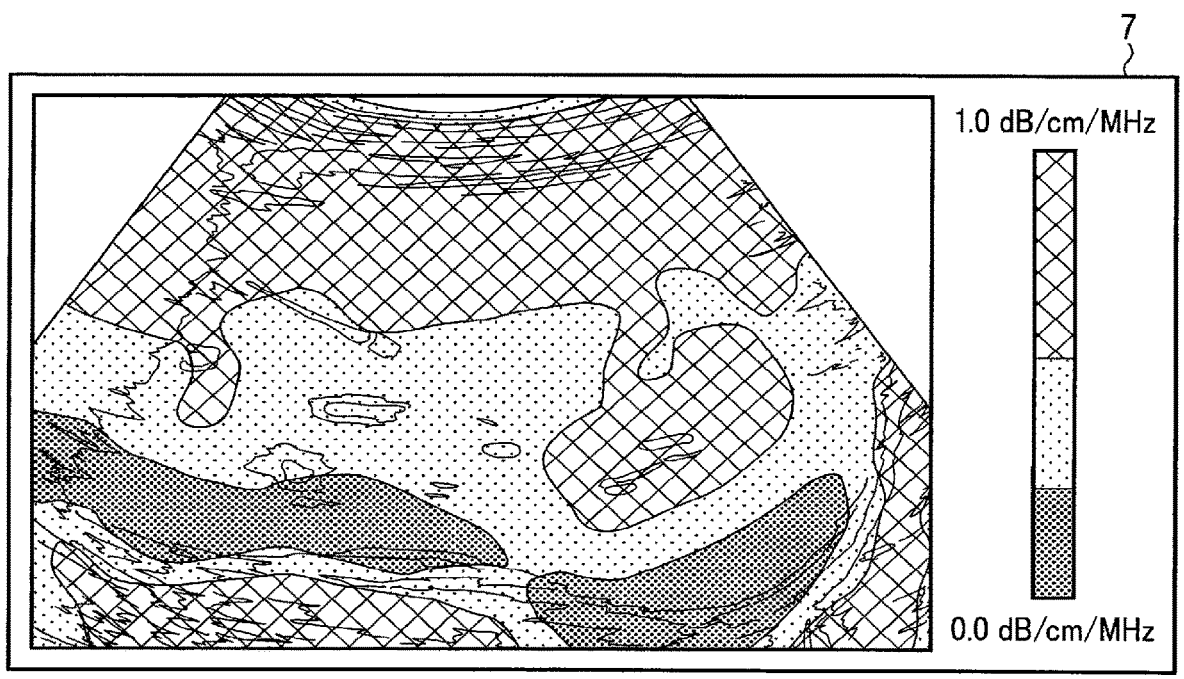
F I G. 11

MEDICAL DIAGNOSTIC APPARATUS AND MEDICAL ANALYSIS METHOD

CROSS-REFERENCE TO RELATED APPLICATIONS

This application is based upon and claims the benefit of priority from the prior Japanese Patent Application No. 2016-047833, filed Mar. 11, 2016, the entire contents of which are incorporated herein by reference.

FIELD

Embodiments described herein relate generally to a medical diagnostic apparatus, which scans the inside of the living body to create a tomographic image of an organ or the like and is related to diagnosis of diseases, and a medical analysis method.

BACKGROUND

An ultrasonic diagnosis apparatus is a diagnosis apparatus which displays an image of intravital information. Compared to other image diagnosis apparatuses such as an X-ray diagnosis apparatus and an X-ray computed tomography (CT) apparatus, the ultrasonic diagnosis apparatus is inexpensive and is free from exposure, and is utilized as a useful medical diagnostic apparatus for observation in real time in a noninvasive manner. The range of applications of the ultrasonic diagnosis apparatus is wide. The ultrasonic diagnosis apparatus is applied to diagnosis of a circulatory organ such as the heart, the abdominal region such as the liver and kidney, peripheral blood vessels, obstetrics and gynecology, and breast cancer.

The ultrasonic diagnosis apparatus usually visualizes the morphology of the body tissue by expressing the magnitude of the amplitude of an ultrasonic reception signal (echo signal) in luminance. However, it has been reported in various reports that an ultrasonic reception signal contains other various types of physical information. Various attempts have been made to clinically apply some of the physical information contained in the ultrasonic reception signal.

For example, a statistical quantity of an amplitude of an echo signal is calculated, and a relationship between a mean value and a variance value is analyzed, whereby a content of a microstructure which is less likely to be visually judged can be quantified. In recent years, there has been used a so-called ultrasonic elastography method of analyzing a local moving amount of an organ in a subject and thereby presenting physical information such as the hardness or elastic modulus of the organ. The ultrasonic elastography method also utilizes phase information contained in an ultrasonic signal before image creation.

A body tissue has specific attenuation characteristics. Ultrasonic waves applied to a subject propagate inside the living body while being attenuated. At this time, when the attenuation amount of the ultrasonic waves having propagated inside the living body is large, there occurs a phenomenon in which a sufficient echo signal cannot be received in the middle of scanning. On the other hand, features of a body tissue are often monitored by observing an attenuation state of the echo signal. For example, there has been known a method of analyzing a change in echo brightness in transmitting and receiving directions to quantify an ultrasonic attenuation amount of a target object. Taking the liver as an example, usefulness is expected, particularly in quantitative diagnosis of fatty liver. Specifically, a subject in which an echo signal is extremely reduced is presumed to be a fatty liver containing many fat droplets in the liver. Similar results may be obtained in a case of liver cirrhosis.

Thus, a plurality of methods for quantitatively diagnosing the ultrasonic attenuation amount have been proposed. For example, a plurality of ultrasonic pulses having different center frequencies are transmitted and received, and a plurality of obtained signals are compared with regard to how much the intensities of the signals change in a depth direction. There is a method of estimating the attenuation amount specific to a subject based on this comparison. It is known that the ultrasonic attenuation amount inside the living body is different depending on frequencies. Thus, a value specific to a target tissue is obtained by comparing changes in intensities of a plurality of frequency signals. Further, by virtue of the use of a broadband pulse, an effect similar to the above effect can be obtained by transmitting and receiving an ultrasonic sound once per one of ultrasonic transmitting and receiving directions.

However, in this method, since a signal of a high frequency (harmonic) component is generated when a signal in a low frequency region propagates in a tissue, it is considered that the generated high frequency component becomes an error when the attenuation amount specific to a subject is estimated. Thus, there has been also proposed a method of transmitting two pulses, in which positive and negative of a waveform of a transmitted ultrasonic wave are inverted, to a subject in a single ultrasonic transmitting direction, performing a difference operation on an obtained reception signal, and thereby removing a high frequency component generated during propagation of an ultrasonic wave.

Further, there has been proposed that a color display reflecting the magnitude of the attenuation amount is performed using the obtained signals of frequency components. For example, different color phases are assigned to the attenuation amounts corresponding to the respective frequency components and are superposed on a B mode image. Consequently, user can visually grasp the magnitude of the attenuation amount with high accuracy by watching a magnitude of a change in color phase in a depth direction. A similar effect can be obtained by performing a color mapping according to a signal intensity difference between two different frequency components. Since an attenuation constant at each point in a cross section is obtained by differentiating the signal intensity difference between two frequency components in the depth direction, the magnitude of the attenuation constant can be colored and displayed.

In all of the methods described in the prior art, the attenuation amount is estimated by calculating the signal intensity of a reception signal or a change in frequency characteristics in the depth direction. The estimation of the attenuation amount is based on the fact that composition and distribution of a scatterer are uniform in the depth direction. However, many different tissues mixedly exist in an actual living body, whereby the living body has a complicated structure. Thus, there are few portions constituted of the uniform scatterers as described above. For example, in the liver, even if there is a portion looking like a uniform speckle in the range of several centimeters, when a focusing range is widened, structures that can be visually recognized, such as blood vessels, an abdominal wall, and a gall bladder, enter a focusing region.

In such structures, brightness of a signal is significantly different from a peripheral uniform substantial portion, and in addition, the reflection characteristics are also different.

Thus, it is considered that the frequency component included in a reception signal is significantly different. Accordingly, in both the method of analyzing the change in brightness and the method of analyzing the frequency component, when the structure, as described above, having characteristics different from the periphery is included in an analysis target region, assumption as a premise of the estimation of the attenuation amount is not established. Consequently, there is a problem that although some numeric values can be calculated in the analysis target region, the calculated values have low reliability.

Namely, in both of the above methods, when a remarkable structure is included in the analysis target region, a brightness distribution and frequency characteristics near the structure are different from the periphery, so that the attenuation amount sometimes cannot be accurately calculated.

For example, as shown in FIG. 11, an extremely high or low attenuation amount value is calculated in a region including, in the analysis target range, a portion exhibiting reflection characteristics and scattering characteristics different from the parenchyma of the liver, like an abdominal wall and a diaphragm. In such a case, the calculated attenuation amount value is considered to be not a result representing the attenuation amount of a target object but an artifact generated by a structure.

From the above, for quantification of the attenuation amount with high accuracy, in a clinical field, there is required a procedure in which a cross section being as inconspicuous in a structure as possible is set, and a uniform region is selected from the set cross section to set the analysis target region. However, judgement in the setting of the analysis target region is left to an operator's subjective view. Thus, there is a problem that the accuracy of the setting of the analysis target region and reproducibility cannot be secured. In addition, it is sometimes difficult to select a region suitable for analysis, and to make matters worse, it takes a long time, so that there is a problem that this is a burden for an operator. Namely, it is a burden for the operator to draw a cross-section avoiding a structure or select a uniform region in which a quantification result is likely to be reliable in quantification, and highly accurate diagnosis may be difficult.

BRIEF DESCRIPTION OF THE DRAWINGS

FIG. 1 is a configuration diagram showing a configuration of an ultrasonic diagnosis apparatus as a medical diagnostic apparatus according to the present embodiment.

FIG. 4 is a view showing an attenuation superimposition image according to the present embodiment displayed on a monitor, together with a legend.

FIG. 9 is a view showing a second application of the present embodiment and showing an example in which representative values and the ranks of reliability corresponding to the names of the measurements ROI and an attenuation superimposition image on which the measurements ROI are superimposed are displayed on the monitor.

FIG. 11 is a view according to the prior art.

DETAILED DESCRIPTION

Figure 2:
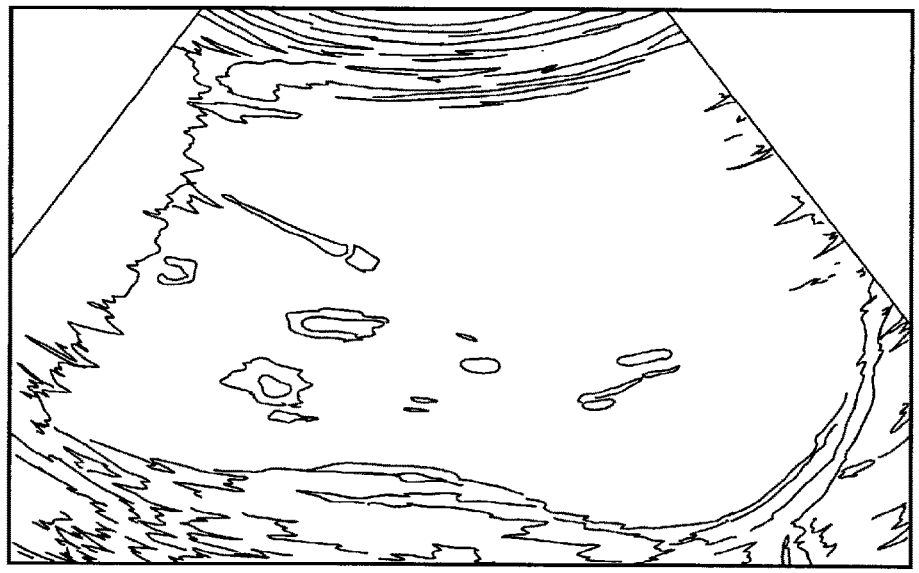
FIG. 2 is a B-mode image according to the present embodiment on which a variance ratio $R_\tau$ is to be superimposed in the color phase corresponding to a value of the variance ratio $R_\tau$.

In general, according to one embodiment, a medical diagnostic apparatus includes processing circuitry and display circuitry. The processing circuitry estimates a position of a structure in a subject based on data obtained by scanning with respect to the subject and analyzes tissue characterization in the subject. The display circuitry displays an analysis result of the tissue characterization obtained by the processing circuitry with respect to a plurality of positions in the subject except for the estimated structure position.

Hereinafter, a medical diagnostic apparatus according to the present embodiment will be described with reference to the drawings. The medical diagnostic apparatus according to the present embodiment may be any apparatus as long as it is noninvasive (for example, a magnetic resonance imaging (MRI) apparatus). In order to specifically describe the medical diagnostic apparatus according to the present embodiment, the medical diagnostic apparatus will be described as an ultrasonic diagnosis apparatus. Note that the same reference numerals in the following description denote constituent elements having substantially the same configurations, and a repetitive description will be made only when required.

FIG. 1 is a configuration diagram showing a configuration of an ultrasonic diagnosis apparatus 1 as the medical diagnostic apparatus according to the present embodiment. As shown in FIG. 1, the ultrasonic diagnosis apparatus 1 has an ultrasonic probe 3, an input apparatus 5, a monitor 7, and an apparatus body 9. In addition, the ultrasonic diagnosis apparatus 1 may be connected to a biological signal measurer (not shown) typified by an electrocardiograph, phonocardiograph, sphygmograph, or respiration sensor, an external storage apparatus (not shown), and a network via interface circuitry 27.

The ultrasonic probe 3 has a plurality of piezoelectric transducers, a matching layer, and a backing material provided on the back face side of the piezoelectric transducers. The piezoelectric transducers are acoustic/electric reversible conversion elements such as piezoelectric ceramic elements.

The plurality of piezoelectric transducers are arranged in parallel and mounted on the distal end of the ultrasonic probe 3. Assume that in the following description, one piezoelectric transducer forms one channel. Each piezoelectric transducer generates an ultrasonic wave in response to a drive signal supplied from ultrasonic transmission circuitry 11 to be described later. When ultrasonic waves are transmitted to a subject P via the ultrasonic probe 3, the transmitted ultrasonic waves (hereinafter referred to as the transmission ultrasonic waves) are reflected by a discontinuity surface of acoustic impedance of a living body tissue in the subject.

The piezoelectric transducers receive the reflected ultrasonic waves and generate an echo signal. The amplitude of the echo signal depends on an acoustic impedance difference on the discontinuity surface as a boundary concerning the reflection of the ultrasonic waves. In addition, the frequency of the echo signal generated when transmission ultrasonic waves are reflected by a moving blood flow and the surface of the cardiac wall or the like shifts depending on the velocity component of the moving body (the blood flow and the surface of the cardiac wall) in the ultrasonic transmitting direction due to the Doppler effect.

Hereinafter, the ultrasonic probe 3 will be described as a probe which two-dimensionally scans a scanned region with a one-dimensional array constituted of one-dimensionally arranged piezoelectric transducers. The ultrasonic probe 3 may be a mechanical four-dimensional probe which executes three-dimensional scanning by swinging a one-dimensional array in a direction perpendicular to the array direction of a plurality of transducers. The ultrasonic probe 3 is not limited to a mechanical four-dimensional probe and may be a two-dimensional array probe.

The matching layer is provided on the ultrasonic wave radiation surface side of the piezoelectric transducers to improve the efficiency of transmission and reception of ultrasonic waves to and from the subject P. The backing material prevents ultrasonic waves from propagating backward from the piezoelectric transducers.

The input apparatus 5 is connected to the apparatus body 9 via the interface circuitry 27. The input apparatus 5 includes various types of switches, buttons, a trackball, a mouse, and a keyboard which are used to input, to the apparatus body 9, various types of instructions and conditions, an instruction to set a region of interest (ROI), various types of image quality conditions, setting instructions, and the like from an operator. The input apparatus 5 may include a touch pad on which an operation surface is touched to perform input operation, a touch panel display in which a display screen and the touch pad are integrated, and microphone. The input apparatus 5 corresponds to an input portion or input interface circuitry.

The input apparatus 5 inputs a start instruction (hereinafter referred to as an attenuation quantification start instruction) for executing a function (hereinafter referred to as a structure estimation function) of comprehensively executing a setting function 291 to be described later and an estimation function 293 to be described later and subsequently executing a function (hereinafter referred to as a tissue characterization analysis function) of comprehensively executing a gain reverse correction function 295 to be described later, a sound field characteristic correction function 297 to be described later, and an analysis function 299 to be described later. At this time, a signal concerning the input of the attenuation quantification start instruction is output to processing circuitry 29 to be described later.

The input apparatus 5 is not limited to an input device provided with only physical operation parts such as a mouse and a keyboard. Examples of the input apparatus 5 include an electric signal processing circuit which receives an electric signal corresponding to an input operation from an external input device provided separately from the ultrasonic diagnosis apparatus 1 and outputs the received electric signal to various circuits.

The monitor 7 displays morphological information in the living body, blood flow information, and the like as images based on video signals output from image generating circuitry 19, image compositing circuitry 23, and so on. The monitor 7 displays analysis results obtained by the analysis function 299. For example, a CRT display, a liquid crystal display, an organic EL display, an LED display, a plasma display, or any other display known in the relevant technical field can be suitably used as the monitor. The monitor 7 corresponds to a display unit or display circuitry.

The apparatus body 9 has ultrasonic transmitting circuitry 11, ultrasonic receiving circuitry 13, B-mode processing circuitry 15, Doppler processing circuitry 17, image generating circuitry 19, an image memory 21, image compositing circuitry 23, storage circuitry 25, interface circuitry 27, and processing circuitry (central processing unit) 29.

The ultrasonic transmitting circuitry 11 has a pulse generator 111, transmission delay circuitry 113, and pulser circuitry 115. The ultrasonic transmitting circuitry 11 is an example of an ultrasonic transmission unit and may have a processor. The pulse generator 111 repeatedly generates rate pulses for the formation of transmission ultrasonic waves at a predetermined rate frequency fr Hz (period: 1/fr sec). The generated rate pulses are distributed to channel counts and sent to the transmission delay circuitry 113.

The transmission delay circuitry 113 gives each rate pulse a delay time (hereinafter referred to as a transmission delay time) necessary to focus a transmission ultrasonic wave into a beam and determine transmission directivity for each of the plurality of channels. The storage circuitry 25 stores the transmission direction of transmission ultrasonic waves or the transmission delay time concerning the transmission direction (hereinafter referred to as a transmission delay pattern). The processing circuitry 29 refers to the transmission delay pattern stored in the storage circuitry 25 when ultrasonic waves are transmitted.

The pulser circuitry 115 applies a voltage pulse (drive signal) to each of the transducers of the ultrasonic probe 3 at the timing based on this rate pulse. According to this constitution, an ultrasonic beam is transmitted to the subject P.

The ultrasonic transmitting circuitry 11 transmits ultrasonic waves (hereinafter referred to as ultrasonic waves for attenuation quantification) to the subject P based on attenuation quantification conditions in response to generation of B-mode data to be described later corresponding to one frame. The attenuation quantification conditions are transmission conditions for generation of the ultrasonic waves for attenuation quantification and reception conditions for reception of the ultrasonic waves for attenuation quantification. The transmission conditions include a transmission center frequency of the ultrasonic wave for attenuation quantification and a transmission bandwidth of the ultrasonic wave for attenuation quantification. The reception conditions include a reception center frequency of the ultrasonic wave for attenuation quantification and a reception bandwidth of the ultrasonic wave for attenuation quantification. The attenuation quantification conditions are stored in the storage circuitry 25.

The transmission conditions are not limited to the above two kinds of conditions and may include a condition where a plurality of ultrasonic waves for attenuation quantification having different frequencies are transmitted to one scanning line. Alternatively, the transmission conditions may include a condition where two ultrasonic waves for attenuation quantification whose phases are inverted are transmitted to one scanning line. The transmission center frequency in the transmission conditions is higher than the transmission center frequency of an ultrasonic wave for B-mode, for example. The bandwidth in the transmission conditions (hereinafter referred to as a narrow band) is narrower than the bandwidth of the ultrasonic wave for B-mode.

In response to the attenuation quantification start instruction from an operator via the input apparatus 5, the attenuation quantification conditions are read from the storage circuitry 25 to the processing circuitry 29. The ultrasonic transmitting circuitry 11 is controlled by the processing circuitry 29 in accordance with the transmission conditions in the attenuation quantification conditions. For example, the ultrasonic transmitting circuitry 11 transmits a plurality of ultrasonic waves having different frequencies to the subject P via the ultrasonic probe 3 in accordance with the transmission conditions in ultrasonic scanning. The ultrasonic transmitting circuitry 11 transmits an ultrasonic wave in the band narrower than the frequency band in the ultrasonic transmission concerning the B-mode to the subject P via the ultrasonic probe 3 in accordance with the transmission conditions in ultrasonic scanning.

The ultrasonic receiving circuitry 13 has a preamplifier 131, an analog to digital (hereinafter referred to as A/D) converter (not shown), reception delay circuitry 133, and an adder 135. The ultrasonic receiving circuitry 13 is an example of an ultrasonic reception unit and may have a processor. The preamplifier 131 amplifies an echo signal from the subject P received via the ultrasonic probe 3 for each channel. The A/D converter converts the received echo signal having been amplified into a digital signal. An analog gain is given as STC (sensitive time control) or TGC (time gain control) to an analog signal before A/D conversion.

The reception delay circuitry 133 gives the received echo signal having been converted into a digital signal a delay time (hereinafter referred to as a reception delay time) necessary to determine reception directivities. The reception delay circuitry 133 is a digital beam former, for example. A digital gain is given as STC or TGC to a digital signal output from the reception delay circuitry 133. The storage circuitry 25 to be described later stores the reception direction of an echo signal or the reception delay time concerning the reception direction (hereinafter referred to as a reception delay pattern). The processing circuitry 29 refers to the reception delay pattern stored in the storage circuitry 25 as when ultrasonic waves are transmitted.

Due to attenuation of an ultrasonic wave in a subject, a signal due to a reflected wave becomes faint as it approaches a depth in the subject. Thus, the analog gain and the digital gain are gains which further amplify the amplitude of a signal due to an ultrasonic wave reflected in the depth in the subject in order to compensate this attenuation.

The adder 135 adds a plurality of echo signals to which the delay times are given. With this addition processing, the ultrasonic receiving circuitry 13 generates a reception signal in which a reflection component from a direction corresponding to the reception directivity is enhanced. The transmission directivity and the reception directivity determine the comprehensive directivity of ultrasonic transmission/reception. This comprehensive directivity determines an ultrasonic beam (so-called "ultrasonic scanning line").

The ultrasonic receiving circuitry 13 receives an ultrasonic wave for attenuation quantification in accordance with the reception conditions in the attenuation quantification conditions. The reception center frequency in the reception conditions is a frequency being substantially the same as the transmission center frequency of an ultrasonic wave for attenuation quantification and is constant without changing with respect to a depth direction in a scanned region. The reception bandwidth in the reception conditions is a bandwidth being substantially the same as the narrow band. The ultrasonic receiving circuitry 13 is controlled by the processing circuitry 29 in accordance with the reception conditions in the attenuation quantification conditions.

Specifically, the ultrasonic receiving circuitry 13 receives a reflected wave of an ultrasonic wave for attenuation quantification transmitted to the subject P in accordance with the reception conditions in response to the generation of the B-mode data to be described later corresponding to one frame. The ultrasonic receiving circuitry 13 generates reception data for attenuation quantification based on the reception of the reflected wave of the ultrasonic wave for attenuation quantification. The ultrasonic transmitting circuitry 11 outputs the reception data for attenuation quantification to the B-mode processing circuitry 15. The ultrasonic transmitting circuitry 11 may output the reception data for attenuation quantification to the processing circuitry 29 and the storage circuitry 25.

The B-mode processing circuitry 15 includes an envelope detector and a logarithmic converter (neither of which is shown). The B-mode processing circuitry 15 is an example of a B-mode processing unit and has a processor. The envelope detector executes envelope detection of the reception signal output from the ultrasonic receiving circuitry 13. The envelope detector outputs the envelope-detected signal to the logarithmic converter to be described later. The logarithmic converter relatively enhances a weak signal by logarithmically converting the envelope-detected signal. The B-mode processing circuitry 15 generates a signal value (B-mode data) for each depth on each scanning line and in each ultrasonic transmission/reception based on the signal enhanced by the logarithmic converter.

The B-mode data corresponds to data in which the strength of a signal output from the logarithmic converter is expressed as a luminance. An output from the B-mode processing circuitry 15 is output to the image generating circuitry 19. The output from the B-mode processing circuitry 15 is displayed as a B-mode image, in which strength of a reflected wave is expressed as a luminance, on the monitor 7. The B-mode processing circuitry 15 generates B-mode data for attenuation quantification in accordance with the above processing procedure based on the reception data for attenuation quantification. The B-mode processing circuitry 15 outputs the B-mode data for attenuation quantification to the processing circuitry 29 and the storage circuitry 25.

When the ultrasonic probe 3 is a mechanical four-dimensional probe or two-dimensional array probe, the B-mode processing circuitry 15 may generate three-dimensional B-mode data comprising a plurality of signal values respectively correspondingly arranged in the azimuth direction, elevation direction, and depth direction (range direction) in a scanned region. The range direction is the depth direction on a scanning line. The azimuth direction is, for example, an electronic scanning direction along the array direction of piezoelectric transducers in a one-dimensional array. The elevation direction is, for example, a mechanical swinging direction of the one-dimensional array.

The three-dimensional B-mode data may be data obtained by arranging a plurality of pixel values, a plurality of luminance values, or the like in the azimuth direction, the elevation direction, and the range direction, respectively, along scanning lines. The three-dimensional B-mode data may be data concerning ROI previously set in a scanned region. The B-mode processing circuitry 15 may generate volume data instead of the three-dimensional B-mode data. Hereinafter, data items generated by the B-mode processing circuitry 15 will be collectively referred to as B-mode data.

The Doppler processing circuitry 17 frequency-analyzes velocity information from the echo signal received from the ultrasonic receiving circuitry 13. The Doppler processing circuitry 17 is an example of a Doppler processing unit and has a processor. The Doppler processing circuitry 17 extracts a blood flow, tissue, and contrast medium echo component by the Doppler effect from the echo signal received from the ultrasonic receiving circuitry 13. The Doppler processing circuitry 17 obtains blood flow information such as a mean velocity, variance, and power at multiple points on a scanning line. The Doppler processing circuitry 17 outputs the obtained blood flow information to the image generating circuitry 19. The output from the Doppler processing circuitry 17 is color-displayed as a Doppler waveform image, a mean velocity image, a variance image, a power image, or a combination image thereof on the monitor 7.

The Doppler processing circuitry 17 includes a mixer, a low pass filter (hereinafter referred to as an LPF), and velocity/variance/power computation circuitry (none of which are shown). The mixer multiplies the reception signal output from the ultrasonic receiving circuitry 13 by a reference signal having a frequency $f_0$ equal to the transmission frequency. This multiplication obtains a signal having a component with a Doppler shift frequency $f_d$ and a signal having a frequency component of $(2f_0+f_d)$. The LPF removes a signal of a high-frequency component $(2f_0+f_d)$ from signals having two types of frequency components from the mixer. The Doppler processing circuitry 17 generates a Doppler signal having the component with the Doppler shift frequency $f_d$ by removing the signal of the high-frequency component $(2f_0+f_d)$.

The Doppler processing circuitry 17 may use a quadrature detection scheme to generate Doppler signals. In this case, a reception signal (RF signal) is subjected to quadrature detection to be converted into an IQ signal. A Doppler processing unit 142 generates a Doppler signal having the component with the Doppler shift frequency $f_d$ by applying complex Fourier transform to the IQ signal. Doppler signals are, for example, Doppler components based on a blood flow, tissue, and contrast medium.

The velocity/variance/power computation circuitry includes an MTI (Moving Target Indicator) filter, an LPF filter, and an autocorrelation computation unit (none of which are shown). This circuitry may include a cross-correlation computation unit instead of an autocorrelation computation unit. The MTI filter removes a Doppler component (a clutter component) caused by the respiratory movement or pulsatory movement of an organ or the like from a generated Doppler signal. The MTI filter is used to extract a Doppler component (hereinafter referred to as a blood flow Doppler component) concerning a blood flow from a Doppler signal. The LPF is used to extract a Doppler component (hereinafter referred to as a tissue Doppler component) concerning the movement of the tissue from a Doppler signal.

The autocorrelation computation unit calculates autocorrelation values concerning a blood flow Doppler signal and a tissue Doppler component. The autocorrelation computation unit calculates the mean velocity values of the blood flow and the tissue, variances, the reflection intensities (powers) of Doppler signals, and the like based on the calculated autocorrelation values. The velocity/variance/power computation circuitry generates color Doppler data at the respective positions in a predetermined region based on the mean velocity values of the blood flow and the tissue, the variances, the reflection intensities of the Doppler signals, and the like based on a plurality of Doppler signals. Hereinafter, Doppler signals and color Doppler data will be collectively referred to as Doppler data.

The image generating circuitry 19 includes a digital scan converter (hereinafter referred to as a DSC) (not shown). The image generating circuitry 19 is an example of an image generating unit and has a processor. The image generating circuitry 19 executes coordinate transformation processing (resampling) for the DSC. The coordinate transformation processing is to transform, for example, a scanning line signal string for ultrasonic scanning, which is formed from B-mode data and Doppler data, into a scanning line signal string in a general video format typified by a TV format.

The image generating circuitry 19 generates an ultrasonic image as a display image by executing coordinate transformation processing. Specifically, the image generating circuitry 19 generates a B-mode image based on B-mode data. The image generating circuitry 19 generates an attenuation B-mode image based on B-mode data for attenuation quantification. The B-mode image and the attenuation B-mode image have pixel values (luminance value) reflecting characteristics of an ultrasonic probe such as convergence of sonic waves, sound field characteristics of an ultrasonic beam (for example, a transmission/reception beam), and the like. For example, in the B-mode image, the luminance near the focus of ultrasonic waves in a scanned region is relatively higher than that in a non-focus portion.

The image generating circuitry 19 generates a Doppler image such as a mean velocity image, a variance image, and a power image based on Doppler data. The image generating circuitry 19 further generates an attenuation quantification image showing the ultrasonic attenuation amount at each position in a partial region in a scanned region, based on the analysis results analyzed by the analysis function 299.

The image memory 21 stores data (hereinafter referred to as image data) corresponding to a generated ultrasonic mage (a B-mode image, mean velocity image, variance image, power image, or attenuation quantification image). The image data stored in the image memory 21 is read out in accordance with an instruction issued by an operator via the input apparatus 5. The image memory 21 is, for example, a memory which stores ultrasonic images corresponding to a plurality of frames immediately before freezing. When the images stored in this cine memory are continuously displayed (cine-displayed) at a predetermined frame rate, a moving ultrasonic image is displayed on the monitor 7.

The image memory 21 is realized by, for example, an integrated circuit memory (such as a random access memory (RAM) and a read-only memory (ROM)). The image memory 21 may be realized by any storage apparatus in addition to the above integrated circuit memories.

The image compositing circuitry 23 composites character information of various parameters, scale marks, and the like on an ultrasonic image. The image compositing circuitry 23 is an example of an image compositing unit and has a processor. The image compositing circuitry 23 outputs the composited ultrasonic image to the monitor 7 to be described later. The image compositing circuitry 23 generates an attenuation superimposition image formed by positioning and superimposing an attenuation quantification image on a B-mode image. The image compositing circuitry 23 outputs the generated attenuation superimposition image to the monitor 7.

The storage circuitry 25 is a storage apparatus such as an HDD (hard disk drive), SSD (solid state drive), or an integrated circuit memory (such as RAM or ROM) storing various kinds of information. The storage circuitry 25 corresponds to a storage unit. The storage circuitry 25 may be realized by a drive apparatus which reads and writes various kinds of information from and in a CD-ROM drive, a DVD drive, or the like. Further, the storage circuitry 25 may be realized by a drive apparatus which reads and writes various kinds of information from and in portable storage media such as magnetic disks (such as Floppy (trademark) disks), optical disks (such as CD-ROMs, DVDs, and MOs), and semiconductor memories.

The storage circuitry 25 stores a plurality of reception delay patterns and a plurality of transmission delay patterns with different focus depths. The storage circuitry 25 stores a control program for the ultrasonic diagnosis apparatus 1, a diagnosis protocol, and a medical analysis program to be described later. The storage circuitry 25 stores various data groups such as ultrasonic transmission/reception conditions and diagnosis information (such as patient ID and doctor's opinions). The storage circuitry 25 stores reception signals generated by the ultrasonic receiving circuitry 13, the B-mode data generated by the B-mode processing circuitry 15, the Doppler data generated by the Doppler processing circuitry 17, and the analysis data showing the analysis results obtained by the analysis function 299.

Further, the storage circuitry 25 stores a program (hereinafter referred to as a structure estimation program) concerning the sizes and setting positions of a plurality of regions set in a scanned region (attenuation B-mode image) concerning collection of B-mode data for attenuation quantification and execution of a structure estimation function. The storage circuitry 25 stores a threshold (hereinafter referred to as a structure determination threshold) referred in the structure estimation function. The storage circuitry 25 stores reverse correction data used in the gain reverse correction function 295, sound field characteristic correction data used in the sound field characteristic correction function 297, a program (hereinafter referred to as a tissue characterization analysis program) concerning execution of the tissue characterization analysis function, and so on. Hereinafter, the structure estimation program and the tissue characterization analysis program will be collectively referred to as a medical analysis program.

The storage circuitry 25 may store a correspondence table (hereinafter referred to as a reverse correction correspondence table) instead of the reverse correction data. The storage circuitry 25 may store a correspondence table (hereinafter referred to as a sound field characteristic correction correspondence table) instead of the sound field characteristic correction data.

The reverse correction data is data used for cancelling an analog gain and a digital gain applied to data (reception signal or reception data) obtained by ultrasonic scanning by the STC or the TGC. Specifically, the reverse correction data is data showing a response in a depth direction of a gain applied to the data obtained by ultrasonic scanning. Namely, when the reverse correction data is applied to the B-mode data, the gain corrected B-mode data is converted into the B-mode data before gain correction.

The reverse correction correspondence table is a correspondence table used for cancelling gain correction according to the STC or the TGC. Specifically, the reverse correction correspondence table is a correspondence table showing the response in the depth direction of the gain applied to the data obtained by ultrasonic scanning and a correspondence table used for converting the B-mode data after gain correction into the B-mode data before gain correction.

The sound field characteristic correction data is data used for cancelling dependency of the sound field characteristics in the B-mode data before gain correction. Namely, when the sound field characteristic correction data is applied to the B-mode data, the B-mode data depending on the sound field characteristics is converted into the B-mode data not depending on the sound field characteristics. The sound field characteristic correction correspondence table is a correspondence table used for cancelling the dependency of the sound field characteristics in the B-mode data. Specifically, the sound field characteristic correction correspondence table is a correspondence table used for converting the B-mode data depending on the sound field characteristics into the B-mode data not depending on the sound field characteristics.

The sound field characteristic correction data and the sound field characteristic correction correspondence table correspond to, for example, a distribution of pixel values (or luminance values) in the depth direction obtained when ultrasonic scanning is executed with respect to an object in which an ultrasonic wave is not attenuated and which has uniform scatterers. The sound field characteristic correction data and the sound field characteristic correction correspondence table are previously generated based on actual measured data obtained by executing ultrasonic scanning with respect to a uniform phantom in which an ultrasonic wave is not attenuated.

The sound field characteristic correction data and the sound field characteristic correction correspondence table may be generated by differentiating an ultrasonic attenuation due to a phantom, having a constant attenuation with respect to an ultrasonic wave, from actual measured data actually measured by ultrasonic scanning with respect to this phantom. The sound field characteristic correction data and the sound field characteristic correction correspondence table may be generated by other means such as simulation.

The storage circuitry 25 stores various images such as a B-mode image, a mean velocity image, a variance image, a power image, an attenuation quantification image, and an attenuation superimposition image. The storage circuitry 25 stores a plurality of color phases corresponding to a plurality of attenuation constants to be described later. The storage circuitry 25 stores a predetermined opacity or transparency concerning an attenuation quantification image. The storage circuitry 25 stores a color phase corresponding to a value of a variance ratio to be described later. The storage circuitry 25 may include the above-described image memory 21. When CFAR (Contrast False Alarm Rate) processing is executed as the structure estimation function, the storage circuitry 25 may store a program concerning the CFAR processing.

The interface circuitry 27 is an interface associated with the input apparatus 5, an operation panel (not shown), a network, an external storage apparatus (not shown), and a biological signal measurer (not shown). The data such as ultrasonic images, analysis results, and the like obtained by the apparatus body 9 can be transferred to another apparatus through the interface circuitry 27 and the network. The interface circuitry 27 can download a medical image concerning a subject obtained by another medical image diagnosis apparatus (not shown) through the network. The interface circuitry 27 corresponds to an interface unit and may have a processor.

The processing circuitry 29 has a function as an information processing apparatus (calculator) and is control means (processor) controlling operation of the apparatus body 9 of the ultrasonic diagnosis apparatus 1. The processing circuitry 29 reads out control programs for executing image generation/display and the like from the storage circuitry 25 and executes computation, control, and the like associated with each type of processing. The processing circuitry 29 corresponds to a control unit.

The processing circuitry 29 reads out the attenuation quantification conditions from the storage circuitry 25 in response to the attenuation quantification start instruction. The processing circuitry 29 controls the ultrasonic transmitting circuitry 11 and the ultrasonic receiving circuitry 13 in accordance with the read-out attenuation quantification conditions. Specifically, the processing circuitry 29 controls the ultrasonic transmitting circuitry 11 in accordance with the read-out transmission conditions. According to this constitution, the ultrasonic transmitting circuitry 11 transmits an ultrasonic wave for attenuation quantification to the subject P after generation of the B-mode data corresponding to one frame. The processing circuitry 29 controls the ultrasonic receiving circuitry 13 in accordance with the read-out reception conditions. According to this constitution, the ultrasonic receiving circuitry 13 receives a reflected wave of an ultrasonic wave for attenuation quantification, transmitted to the subject P, in accordance with the reception conditions.

In the present embodiment, the respective processing functions performed by the setting function 291, the estimation function 293, the gain reverse correction function 295, the sound field characteristic correction function 297, and the analysis function 299 are stored in the storage circuitry 25 in the form of computer-executable programs. The processing circuitry 29 is a processor which reads out the programs corresponding to those functions from the storage circuitry 25 to execute the programs and thus to achieve the functions corresponding to the respective programs. In other words, the processing circuitry 29 in a state of reading out each program has each function shown in the processing circuitry 29 of FIG. 1.

There may be a case where each of the above functions is constituted as a program, and each program is executed by one processing circuit, or there may be case where the estimation function is mounted on a dedicated independent program execution circuit. The setting function 291, the estimation function 293, the gain reverse correction function 295, the sound field characteristic correction function 297, and the analysis function 299 of the processing circuitry 29 are respectively examples of a setting unit, an estimation unit, a gain reverse correction unit, a sound field characteristic correction unit, and an analysis unit. In this case, a processor which achieves the structure estimation function may function as a structure estimation unit. Further, a processor which achieves the tissue characterization analysis function may function as a tissue characterization analysis unit.

The term "processor" used in the above description means, for example, CPU, GPU (Graphical Processing Unit), or a circuit such as an application specific integrated circuit (ASIC), a programmable logic device (for example, a simple programmable logic device (SPLD)), a complex programmable logic device (CPLD), and a field programmable gate array (FPGA).

The processor reads out and executes a program stored in storage circuitry 25 and thereby achieves the function. There may be constituted such that the program is directly incorporated in circuitry of the processor instead of being stored in the storage circuitry 25. In this case, the processor reads out and executes the program incorporated in the circuitry and thereby achieves the function. Other circuitry such as the ultrasonic transmitting circuitry 11, the ultrasonic receiving circuitry 13, the B-mode processing circuitry 15, the Doppler processing circuitry 17, the image generating circuitry 19, the image compositing circuitry 23, and the interface circuitry 27 are similarly constituted of electronic circuits of the above processor or the like.

The processing circuitry 29 reads out the medical analysis program from the storage circuitry 25 in response to the attenuation quantification start instruction. The processing circuitry 29 executes the read-out medical analysis program and thereby achieves the structure estimation function and the tissue characterization analysis function. Specifically, the processing circuitry 29 reads out the structure estimation program and the tissue characterization analysis program from the storage circuitry 25. The processing circuitry 29 executes the read-out structure estimation program and thereby estimates a position of a structure in a subject based on the B-mode data for attenuation quantification obtained by ultrasonic scanning using an ultrasonic wave for attenuation quantification.

For example, the processing circuitry 29 executes the read-out tissue characterization analysis program in response to the estimation of the position of the structure and thereby analyzes tissue characterization in a scanned region corresponding to the B-mode data for attenuation quantification. Hereinafter, various functions concerning the estimation of a position of a structure in a subject and various functions concerning the analysis of the tissue characterization will be specifically described.

In the following description, although the setting function 291, the estimation function 293, the gain reverse correction function 295, the sound field characteristic correction function 297, the analysis function 299, and the like are executed in the single processing circuitry 29, a processing circuitry is constituted by combining a plurality of independent processors, and each processor executes a program, whereby various functions may be achieved. The setting function 291, the estimation function 293, the gain reverse correction function 295, the sound field characteristic correction function 297, the analysis function 299, and the like may be achieved by different processing circuitry or processors.

(Structure Estimation Function)

The structure estimation function include a function of evaluating ununiformity at a plurality of positions in a subject based on the B-mode data for attenuation quantification obtained by ultrasonic scanning with respect to the subject P and thereby estimating a position of a structure. As the structure estimation function, there are various methods of estimating a structure. Hereinafter, as one example of such a method, there will be described a method using a mean value of a plurality of pixel values (or luminance values) respectively corresponding to a plurality of pixels included in each of a plurality of regions set in an attenuation B-mode image and variance values.

This method generally uses the fact that in a region having uniform scatterers such as the parenchyma of the liver, frequency distribution (histogram) of the B-mode data for attenuation quantification exhibits Rayleigh distribution. In the region having uniform scatterers, when the frequency distribution of the B-mode data for attenuation quantification follows the Rayleigh distribution, a mean value ($\mu$) and a variance value ($\sigma^2$) due to a plurality of pixel values in this region have the following relationship.

$$\sigma^2=(4/\pi-1)\times\mu^2 \quad (1)$$

When a structure is included in a region concerning calculation of the mean value and the variance value, since scatterers are nonuniform, the variance value of the frequency distribution of the B-mode data for attenuation quantification is larger than the variance value calculated according to the Rayleigh distribution. In addition, the more significantly different characteristics of a structure from the surroundings (for example when the region of the structure corresponds to a calcified region), the larger the variance value. Thus, a presence of a structure in each pixel representing a region can be determined by calculating a variance value in each of a plurality of regions set in a scanned region.

However, since the larger the pixel value, the larger the variance value, the presence of a structure, that is, occurrence of deviation from the Rayleigh distribution obtained in the case of uniform scatterers cannot be determined by simply calculating the variance value itself. Thus, in this embodiment, the Rayleigh distribution having a mean value being the same as a mean value of pixel values in a set region is assumed with respect to the set region. Based on this assumption, there is calculated a ratio (hereinafter referred to as a variance ratio $R_\sigma$) of the variance value $\sigma^2$ of the pixel value in the set region with respect to a variance value $\{(4/\pi-1)\times\mu^2\}$ calculated using the mean value of the pixel values in the set region and the formula (1). Specifically, the variance ratio $R_\tau$ is represented by the following formula.

$$R_\sigma=\sigma^2/\{(4/\pi-1)\times\mu^2\} \quad (2)$$

The molecule ($\sigma^2$) at the right side of the formula (2) is an actually measured variance value calculated from a plurality of pixel values respectively corresponding to a plurality of pixels included in the set region. The denominator $\{(4/\pi-1)\times\mu^2\}$ at the right side of the formula (2) is a variance value in a case where it is assumed that with the use of a mean value $\mu$, calculated from pixel values of variances respectively corresponding to a plurality of pixels included in the set region, and the formula (1), the pixel values in the set region form the Rayleigh distribution.

When the variance ratio $R_\sigma$ is close to 1, the distribution of the pixel values in the set region can be regarded as the Rayleigh distribution. When the variance ratio $R_\tau$ is more than 1, it is estimated that the distribution of the pixel values included in the set region deviates from the Rayleigh distribution, and the set region includes a structure deviated from uniform scatterers. Namely, the variance ratio $R_\sigma$ corresponds to an index of determination of the presence of a structure in the set region.

The processing circuitry 29 achieving the setting function 291 sets a plurality of regions in a scanned region (attenuation B-mode image) in which the B-mode data for attenuation quantification is collected, that is, a scanning region in ultrasonic scanning using ultrasonic waves for attenuation quantification. The set regions have predetermined sizes with each pixel in an attenuation B-mode image as the center (hereinafter referred to as a center pixel) or the center of the gravity. The size of the region set in the attenuation B-mode image may be suitably changed by an instruction from an operator via the input apparatus 5. The processing circuitry 29 may sweep one region for each width of a predetermined pixel and thereby set a plurality of regions in the attenuation B-mode image.

The processing circuitry 29 achieving the estimation function 293 estimates a position of a structure based on a pixel value (or luminance value) corresponding to each of a plurality of pixels included in each of a plurality of set regions. At this time, the pixel value corresponds to the pixel value in the B-mode data for attenuation quantification. The estimation function 293 may use a pixel value in usual B-mode data. Specifically, the processing circuitry 29 calculates a mean value of pixel values (or luminance values) and a variance value in each of a plurality of regions. The processing circuitry 29 calculates the variance ratio $R_\sigma$ based on the mean value and the variance value. The calculated variance ratio $R_\sigma$ may be stored in the storage circuitry 25. The variance ratio $R_\tau$ may be displayed on the monitor 7 while being superimposed on a B-mode image in a scanned region, being the same as the scanned region concerning the variance ratio $R_\sigma$, in color phase corresponding to the value of the variance ratio $R_\sigma$.

Figure 3:
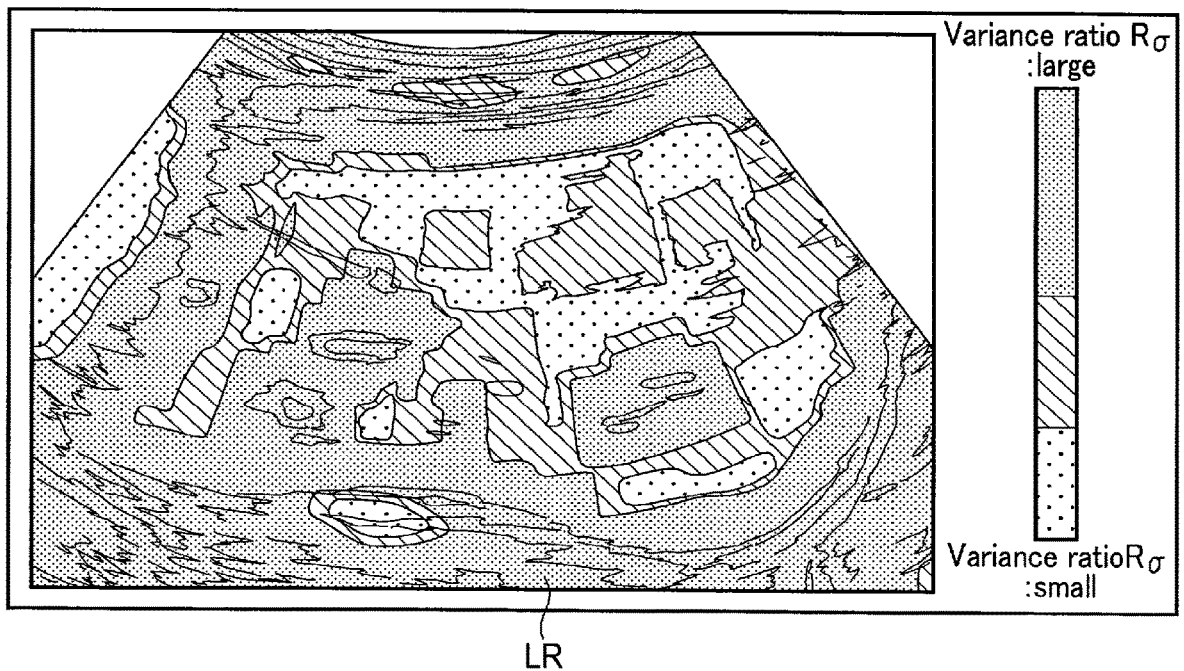
FIG. 3 is a view showing an example of a variance ratio superimposition image in which the variance ratio $R_\tau$ is superimposed on the B-mode image of FIG. 2 in a scanned region being the same as the scanned region concerning the variance ratio $R_\tau$ in the color phase corresponding to the value of the variance ratio $R_\tau$.

FIG. 2 is a B-mode image on which the variance ratio $R_\sigma$ is to be superimposed in the color phase corresponding to the value of the variance ratio $R_\sigma$. The B-mode image shown in FIG. 2 shows a cross section of the liver of the subject P. FIG. 3 is a view showing an example of a variance ratio superimposition image in which the variance ratio $R_\tau$ is superimposed on the B-mode image of FIG. 2 in the same scanned region concerning calculation of the variance ratio $R_\tau$ in the color phase corresponding to the value of the variance ratio $R_\tau$. A difference in hatching in FIG. 3 corresponds to a difference in color phase. Although FIG. 3 shows three types of color phases of the variance ratio $R_\tau$ for ease of illustration of the variance ratio superimposition image, a substantially continuous color phase is actually displayed on the monitor 7, together with a legend showing the color phase of the variance ratio $R_\tau$.

The hatching LR in FIG. 3 shows a region where the variance ratio $R_\tau$ is large. As shown in FIG. 3, in a region of a structure, such as blood vessels, an abdominal wall, or diaphragm, or a region around the structure, the variance ratio $R_\sigma$ is large as compared with the parenchyma of the liver having a uniform speckle. Namely, as seen in FIG. 3, in the region of the structure and the region around the structure, scattering characteristics of ultrasonic waves are ununiform. Thus, the region of the structure and the region around the structure are not appropriate as an analysis target of the ultrasonic attenuation amount.

The processing circuitry 29 makes the calculated variance ratio $R_\tau$ correspond to a position representing the region set by the setting function 291, for example, a position of the center pixel. The processing circuitry 29 reads out the structure determination threshold from the storage circuitry 25. The structure determination threshold is a numerical value being not less than 1. The structure determination threshold may be suitably changed by an instruction from an operator via the input apparatus 5. The processing circuitry 29 compares the read-out structure determination threshold and the variance ratio $R_\sigma$. The processing circuitry 29 estimates the variance ratio $R_\tau$ being larger than the structure determination threshold as a position of a structure.

The processing circuitry 29 achieving the estimation function 293 may output, to the storage circuitry 25, the structure position estimated in a scanned region corresponding to an attenuation B-mode image, that is, the region of the structure. The estimated structure position is used in the tissue characterization analysis function to be described later. The estimated region of the structure corresponds to a region shown by the hatching LR, as shown in FIG. 3, for example.

The method of estimating a structure with the use of a reception signal and the B-mode data for attenuation quantification is not limited to the above method. For example, the structure estimation function may use a presumptive signal (or image) extraction technique referred to as CFAR processing. The term "CFAR processing" is used in the field of radars. In this embodiment, for convenience, the term "CFAR" is used for specific description according to its relevance. However, the term "CFAR processing" is irrespective of a method used in the field of radars or a method strictly using a statistical quantity.

The CFAR processing is executed by the following procedures (1) to (3), for example.

(1) The processing circuitry 29 achieving the setting function 291 sets a region having neighboring pixels near a target pixel Pi for each of the target pixels Pi in an attenuation B-mode image. The region set as the neighboring pixels by the processing circuitry 29 is provided in a cross shape in the attenuation B-mode image. However, arrangement of the neighboring pixels in the set region is not limited to the cross shape, and for example when the time required for arithmetic processing does not cause a problem, there may be a region having any size except for eight pixels adjacent to a target pixel.

The processing circuitry 29 achieving the estimation function 293 calculates a luminance mean value (or pixel mean value) in the set region. At this time, in order to prevent a luminance value (or pixel value) of a target pixel from affecting a mean value, the processing circuitry 29 may calculate the luminance mean value such that the target pixel Pi itself is not included in the calculation.

(2) Next, the processing circuitry 29 subtracts the mean value from the pixel value of the target pixel Pi. The processing circuitry 29 defines the subtraction value as an arithmetic result Ki with respect to a position of the target pixel Pi and allows the storage circuitry 25 to store the arithmetic result Ki. The processing circuitry 29 executes the arithmetic processing with respect to all the target pixels Pi.

(3) The processing circuitry 29 reads out a previously set threshold T from the storage circuitry 25. In this case, the threshold T corresponds to the structure determination threshold and is generally a value different from the structure determination threshold corresponding to the variance ratio $R_o$. The processing circuitry 29 compares the arithmetic result Ki and the threshold T. When Ki≥T, the target pixel Pi is displayed using original luminance (extraction of a structure). On the other hand, when Ki<T, the luminance value of the target pixel Pi is taken to be 0 and is thus not displayed (removal of a structure). The CFAR processing concerning the image can be executed by executing the above processing with respect to all the target pixels Pi.

In the determination in (3), it may be configured such that when Ki≥T, the target pixel Pi is displayed while the luminance is taken to be Ki, and when Ki<T, the luminance value of the target pixel Pi is taken to be 0 and is thus not displayed.

More simply, the structure estimation function may estimate a position of a structure by comparing a mean value of luminance values (or pixel values) in a plurality of regions set in a usual B-mode image, a variance value, a standard deviation, and the like and thresholds used for structure determination corresponding to the respective values.

(Tissue Characterization Analysis Function)

The tissue characterization analysis function is executed by the processing circuitry 29 in accordance with the tissue characterization analysis program. Specifically, the tissue characterization analysis function analyzes tissue characterization with respect to a plurality of positions except for a position of a structure estimated in an attenuation B-mode image based on B-mode data for attenuation quantification. The tissue characterization analysis function has the gain reverse correction function 295, the sound field characteristic correction function 297, the analysis function 299, and a display function (not shown). Hereinafter, each function in the tissue characterization analysis function will be described in detail. The tissue characterization is, for example, a feature quantity concerning an attenuation amount showing a degree of attenuation of an ultrasonic wave for attenuation quantification propagating inside a subject.

The tissue characterization is not limited to the attenuation amount and may be an amount showing characterization of a tissue to be diagnosed, such as modulus of elasticity (Young's modulus), viscosity, and distortion. In this case, the tissue characterization is obtained by an ultrasonic elastography method, for example. The analysis function 299 has various analysis functions concerning a static or dynamic elastography method. In this case, the processing circuitry 29 achieving the analysis function 299 calculates as the tissue characterization an index value (viscosity parameter or elasticity parameter) concerning at least one of viscosity and elasticity of a tissue in a subject.

In a typified ultrasonic elastography method, a tissue in a subject is pressed/released from a surface of the body by the ultrasonic probe 3, whereby relative hardness of the tissue in the subject is visualized based on a magnitude of distortion at each point in a cross section observed during pressing/releasing.

In another typified ultrasonic elastography method, displacement (distortion) of a tissue at each point in a cross section is observed with the lapse of time by applying acoustic radiant power or mechanical vibration to a tissue in the subject P from the body surface of the subject P. Specifically, the dynamic ultrasonic elastography method is a method of obtaining the propagation velocity of shear waves generated by acoustic radiant power or mechanical vibration and thereby obtaining the modulus of elasticity, viscosity, and the like of the tissue to be diagnosed. Ultrasonic waves transmitted and received by the static or dynamic ultrasonic elastography method correspond to ultrasonic waves for attenuation quantification. In this case, as data used in the structure estimation function, B-mode data concerning generation of a B-mode image is used. An image (such as an elasticity image, a viscosity image, and a distortion image) generated by the ultrasonic elastography method corresponds to an attenuation quantification image.

Hereinafter, the tissue characterization analysis function will be described as the function of calculating the attenuation amount as the tissue characterization. Prior to the execution of the gain reverse correction function 295, the processing circuitry 29 estimates data (hereinafter referred to as partial data for attenuation quantification) corresponding to a plurality of positions except for a position of a structure estimated in a scanned region corresponding to an attenuation B-mode image in B-mode data for attenuation quantification.

The processing circuitry 29 achieving the gain reverse correction function 295 reads out reverse correction data from the storage circuitry 25. The processing circuitry 29 subtracts the reverse correction data from the partial data for attenuation quantification corresponding to a plurality of positions except for a position of a structure estimated in a scanned region. According to this constitution, the processing circuitry 29 generates the partial data for attenuation quantification, which is not subjected to gain correction. The processing circuitry 29 may read out the reverse correction correspondence table from the storage circuitry 25. In this case, the processing circuitry 29 converts the partial data for attenuation quantification into the partial data for attenuation quantification before gain correction in accordance with the reverse correction correspondence table. Namely, the gain reverse correction function 295 cancels gain correction with respect to the partial data for attenuation quantification.

By virtue of the gain reverse correction function 295, the processing circuitry 29 restores reception data at the time when the ultrasonic probe 3 has received a reflected wave of an ultrasonic wave for attenuation quantification, that is, the pure strength of a depth-directional ultrasonic signal along the depth direction. If uncorrected partial data for attenuation quantification (raw data) can be output from the ultrasonic receiving circuitry 13, the gain reverse correction function 295 is not required.

The processing circuitry 29 achieving the sound field characteristic correction function 297 reads out sound field characteristic correction data from the storage circuitry 25. The processing circuitry 29 subtracts the sound field characteristic correction data from the partial data for attenuation quantification before gain correction. Consequently, the processing circuitry 29 generates the partial data for attenuation quantification (hereinafter referred to as attenuation data), which is not subjected to gain correction and does not depend on the sound field characteristics. The processing circuitry 29 may read out the sound field characteristic correction correspondence table from the storage circuitry 25. In this case, the processing circuitry 29 converts the partial data for attenuation quantification before gain correction into the attenuation data in accordance with the sound field characteristic correction correspondence table. Namely, the processing circuitry 29 cancels the dependency on the sound field characteristics in the partial data for attenuation quantification before gain correction, based on the sound field characteristics in ultrasonic scanning.

By virtue of the sound field characteristic correction function 297, the processing circuitry 29 eliminates a variation of a pixel value (or luminance value) specific to the shape of an ultrasonic beam and the shape of the ultrasonic probe 3 from B-mode data for attenuation quantification before gain correction. By virtue of this elimination, the processing circuitry 29 generates attenuation rata having a pixel value (or luminance value) reflecting a degree of pure attenuation of an ultrasonic wave due to a tissue in a subject. The attenuation data corresponds to correction data corrected by the gain reverse correction function 295 and the sound field characteristic correction function 297.

The processing circuitry 29 executing the analysis function 299 analyzes the tissue characterization at a plurality of positions in a subject except for an estimated structure position (the positions will be hereinafter referred to as a non-structure region) based on the attenuation data obtained by ultrasonic scanning with respect to the subject P. Namely, the processing circuitry 29 achieving the analysis function 299 calculates the attenuation amount of an ultrasonic wave for attenuation quantification propagating inside a subject.

Specifically, the processing circuitry 29 calculates a differential value along a depth direction in a pixel value (or luminance value) in the non-structure region in attenuation data. The differential value corresponds to, for example, a value obtained by dividing a difference value between pixel values of two pixels adjacent along the depth direction by an interval (distance) between the two pixels in each of a plurality of pixels in the non-structure region.

Subsequently, the processing circuitry 29 multiplies the calculated differential value by ½ while considering two ways of ultrasonic waves. Consequently, the processing circuitry 29 calculates the ultrasonic attenuation amount (dB/cm) concerning the transmission center frequency of an ultrasonic wave for attenuation quantification with respect to a plurality of pixels (positions) included in the non-structure region. Further, the processing circuitry 29 divides the calculated attenuation amount by the transmission center frequency of an ultrasonic wave for attenuation quantification. By virtue of the division, the processing circuitry 29 calculates attenuation constants (dB/cm/Hz) at a plurality of pixels (positions) included in the non-structure region.

The attenuation constant does not depend on the transmission center frequency of an ultrasonic wave for attenuation quantification. Further, the attenuation constant is substantially constant for each of a plurality of pixels (positions) included in the non-structure region. The attenuation constant is a numerical value representing characterization of a tissue to be diagnosed. By virtue of the above various calculations, the processing circuitry 29 generates analysis data (hereinafter referred to as attenuation constant data) showing attenuation constants at a plurality of positions included in the non-structure region. The processing circuitry 29 outputs the attenuation constant data to the image generating circuitry 19, the storage circuitry 25, and so on.

The tissue characterization is not limited to the attenuation constant according to analysis of the luminance value or the pixel value and may be an amount reflecting the attenuation amount according to another analysis. For example, when a plurality of ultrasonic waves for attenuation quantification having different frequencies are transmitted and received to and from one scanning line, the processing circuitry 29 achieving the analysis function 299 executes frequency analysis based on Doppler data at a plurality of positions included in the non-structure region and thereby may calculate a parameter showing the tissue characterization at a plurality of positions included in the non-structure region. Specifically, the processing circuitry 29 calculates as the tissue characterization a difference between attenuation amounts due to a difference in frequency with the use of Doppler data corresponding to each of a plurality of ultrasonic waves for attenuation quantification.

When an ultrasonic wave in the band narrower than the frequency band in the ultrasonic transmission concerning the B-mode is transmitted as the ultrasonic wave for attenuation quantification to the subject P, the processing circuitry 29 executes frequency analysis with respect to data obtained by reception of the ultrasonic wave for attenuation quantification in the narrow band. Subsequently, the processing circuitry 29 calculates the attenuation amount as the tissue characterization, based on the frequency characteristics in the frequency analysis.

The processing circuitry 29 achieving the display function allows the monitor 7 to display the tissue characterization as the analysis result thereon. Specifically, the processing circuitry 29 outputs the attenuation constant data to the image generating circuitry 19. The image generating circuitry 19 generates an attenuation quantification image based on the attenuation constant data. At this time, the processing circuitry 29 controls the image generating circuitry 19 in order to apply color phase corresponding to an attenuation constant in the attenuation quantification image. By virtue of the control, the attenuation quantification image has the color phase corresponding to the attenuation constant.

In a region corresponding to a position of a structure, the attenuation quantification image is in a state of being missed. Namely, the attenuation quantification image corresponding to the region corresponding to the position of the structure does not exist. The image generating circuitry 19 outputs the attenuation quantification image to the image compositing circuitry 23.

The image compositing circuitry 23 executes positioning (registration) between a B-mode image concerning a scanned region being substantially the same as the scanned region concerning collection of B-mode data for attenuation quantification and the attenuation quantification image under control by the processing circuitry 29. The image compositing circuitry 23 converts the attenuation quantification image into a predetermined opacity or transparency under control by the processing circuitry 29.

The image compositing circuitry 23 generates an attenuation superimposition image in which the attenuation quantification image having a predetermined opacity or transparency is superimposed on a B-mode image. The image compositing circuitry 23 composites legends corresponding to color phase of the attenuation constant on the attenuation superimposition image. The image compositing circuitry 23 outputs the attenuation superimposition image on which the legends and so on are composited to the monitor 7.

The monitor 7 displays the attenuation amount as the analysis result at each of a plurality of positions in a subject except for a position of a structure. Specifically, the monitor 7 displays the attenuation superimposition image on which the legends and so on are composited.

FIG. 4 is a view showing an attenuation superimposition image displayed on the monitor 7 together with legends. As shown in FIG. 4, in the attenuation superimposition image, the attenuation quantification image is displayed in a state of being superimposed on a B-mode image at a predetermined opacity or transparency. As shown in FIG. 4, in the attenuation superimposition image, a region including an estimated structure position is a region which has a large variance ratio as shown in FIG. 3 and where the attenuation constant is not calculated, that is, a region where there is no attenuation quantification image. A B-mode image of a back surface is displayed in this region. Namely, the region including the structure position estimated in FIG. 4 includes structures, such as blood vessels, an abdominal wall, and diaphragm, and regions near the structures and is a region where an attenuation quantification image (color image) showing an attenuation constant is not displayed.

Figure 5:
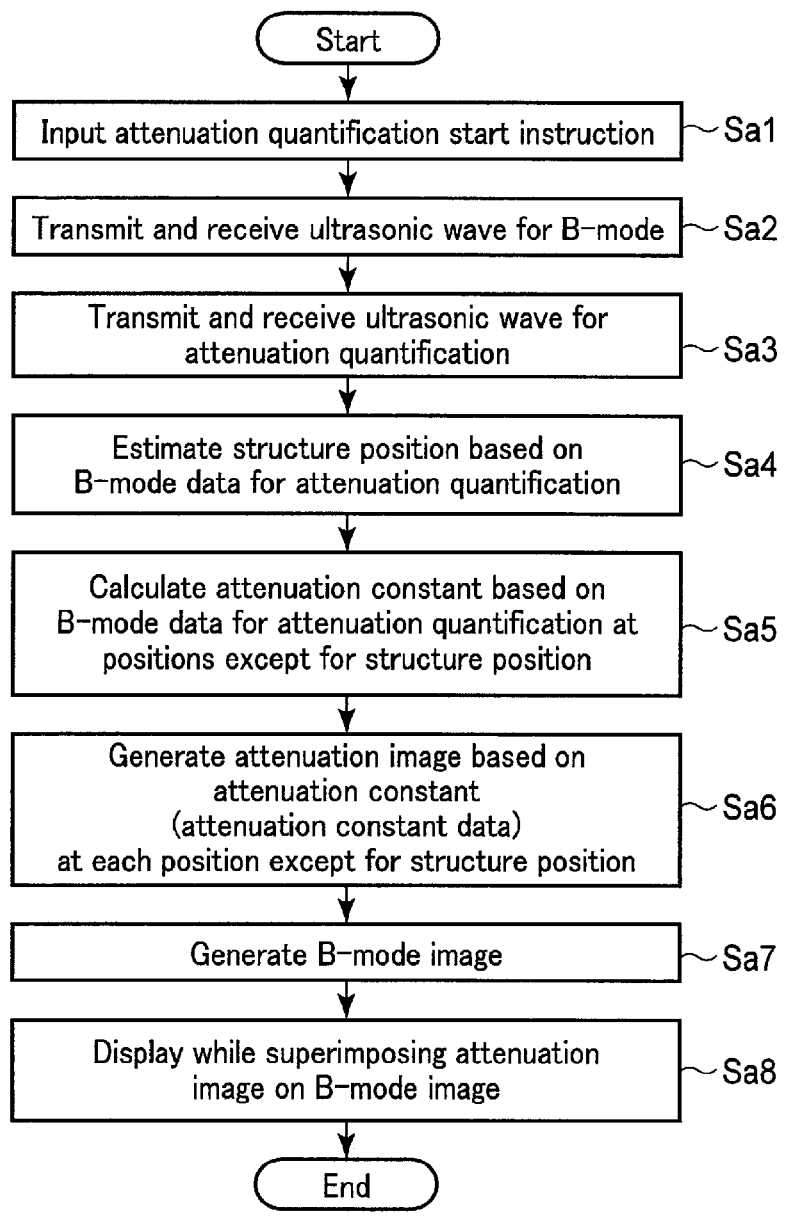
FIG. 5 is a flowchart showing an example of a processing procedure according to the present embodiment concerning a structure estimation function and a tissue characterization analysis function.

Hereinafter, a processing procedure concerning the structure estimation function and the tissue characterization analysis function will be described. FIG. 5 is a flowchart showing an example of the processing procedure concerning the structure estimation function and the tissue characterization analysis function.

The attenuation quantification start instruction is input by the input apparatus 5 (Step Sa1). An ultrasonic wave for B-mode is transmitted and received to and from the subject P in response to the input of the attenuation quantification start instruction (Step Sa2). The processing in Step Sa1 may be executed after the processing in Step Sa2. At this time, an operator inputs the attenuation quantification start instruction when a B-mode image concerning analysis of an attenuation constant is displayed with respect to the subject P. In addition, the storage circuitry 25 may store a B-mode image generated in connection with the processing in Step Sa2 as shown in FIG. 2.

When B-mode data corresponding to one frame, that is, one scanned region is collected, an ultrasonic wave for attenuation quantification is transmitted and received to and from the subject P (Step Sa3). Subsequently, B-mode data for attenuation quantification is generated. A position of a structure is estimated based on the B-mode data for attenuation quantification (Step Sa4). The structure position may be estimated based on the B-mode data generated after the processing in Step Sa2. At this time, a variance ratio superimposition image (see FIG. 3) in which the variance ratio used in the estimation of the structure position is superimposed on the B-mode image may be displayed on the monitor 7.

The tissue characterization (for example, the attenuation constant) at a plurality of positions except for the estimated structure position is calculated based on the B-mode data for attenuation quantification (Step Sa5). By virtue of the processing in Step Sa5, attenuation constant data in a scanned region being substantially the same as a scanned region concerning the B-mode image is generated. An attenuation quantification image is generated based on attenuation constant data showing an attenuation constant at each of a plurality of positions except for a structure position (Step Sa6). B-mode data is generated based on a reception signal received in the processing in Step Sa2. Subsequently, a B-mode image is generated based on the B-mode data (Step Sa7).

The B-mode image and the attenuation quantification image are positioned. In addition, a predetermined opacity or transparency is applied to the attenuation quantification image. An attenuation superimposition image in which the attenuation quantification image having a predetermined opacity or transparency is superimposed on the B-mode image is generated. The attenuation superimposition image is displayed on the monitor 7 (Step Sa8).

(Variation)

A variation differs from the above embodiment in that an attenuation quantification image corresponding to a scanned region concerning collection of B-mode data for attenuation quantification is generated, and the attenuation quantification image at a structure position estimated in the scanned region is not displayed in an attenuation superimposition image. In this variation, the processing of estimating partial data for attenuation quantification in the B-mode data for attenuation quantification is not required.

(Tissue Characterization Analysis Function)

The processing circuitry 29 achieving the gain reverse correction function 295 subtracts reverse correction data from B-mode data for attenuation quantification. According to this constitution, the processing circuitry 29 generates the B-mode data for attenuation quantification before gain correction over the entire scanned region.

The processing circuitry 29 achieving the sound field characteristic correction function 297 subtracts sound field characteristic correction data from the B-mode data for attenuation quantification before gain correction. Consequently, the processing circuitry 29 generates the B-mode data for attenuation quantification (hereinafter referred to as attenuation B-mode data), which is not subjected to gain correction and does not depend on the sound field characteristics.

The processing circuitry 29 executing the analysis function 299 analyzes the tissue characterization in the entire scanned region based on the attenuation B-mode data.

Specifically, the processing circuitry 29 calculates a differential value along a depth direction in a pixel value (or luminance value) in the attenuation B-mode data. The processing circuitry 29 divides a value (attenuation amount), obtained by multiplying the calculated differential value by ½ while considering two ways of ultrasonic waves, by the transmission center frequency of an ultrasonic wave for attenuation quantification. By virtue of the division, the processing circuitry 29 calculates an attenuation constant at each of a plurality of pixels (positions) in a collection region.

By virtue of the above various calculations, the processing circuitry 29 generates analysis data (attenuation constant data) showing an attenuation constant in the entire scanned region. The processing circuitry 29 outputs the attenuation constant data to the image generating circuitry 19 and the storage circuitry 25.

The processing circuitry 29 achieving the display function outputs the attenuation constant data to the image generating circuitry 19. The image generating circuitry 19 generates an attenuation quantification image to which color phase corresponding to an attenuation constant in an attenuation quantification image is applied, based on the attenuation constant data. The size of the attenuation quantification image in this variation approximately corresponds to the size of a scanned region.

The image compositing circuitry 23 converts the attenuation quantification image into a predetermined opacity or transparency under control by the processing circuitry 29. The image compositing circuitry 23 generates an attenuation superimposition image in which the attenuation quantification image having a predetermined opacity or transparency is superimposed on a B-mode image. The processing circuitry 29 controls the image compositing circuitry 23 or the monitor 7 such that in display of the attenuation superimposition image, a partial region of an attenuation quantification image corresponding to a structure position estimated in a scanned region is not displayed. At this time, the monitor 7 displays the attenuation superimposition image in the form shown in FIG. 4, for example. Namely, the monitor 7 displays the analysis results obtained by the analysis function 299 with respect to a plurality of positions in a subject except for the structure position estimated by the estimation function 293.

The processing circuitry 29 may control the image compositing circuitry 23 or the monitor 7 such that the attenuation quantification image is displayed while masking the partial region in predetermined color phase. At this time, the monitor 7 displays the attenuation quantification image while masking the partial region in predetermined color phase.

The image generating circuitry 19 may generate a partial attenuation image in which a partial region of an attenuation quantification image corresponding to a structure position estimated in a scanned region is removed from the attenuation quantification image under control by the processing circuitry 29. At this time, the image compositing circuitry 23 converts the partial attenuation image into a predetermined opacity or transparency under control by the processing circuitry 29. The image compositing circuitry 23 generates an attenuation superimposition image in which the partial attenuation image having a predetermined opacity or transparency is superimposed on a B-mode image. The monitor 7 displays the attenuation superimposition image.

Figure 6:
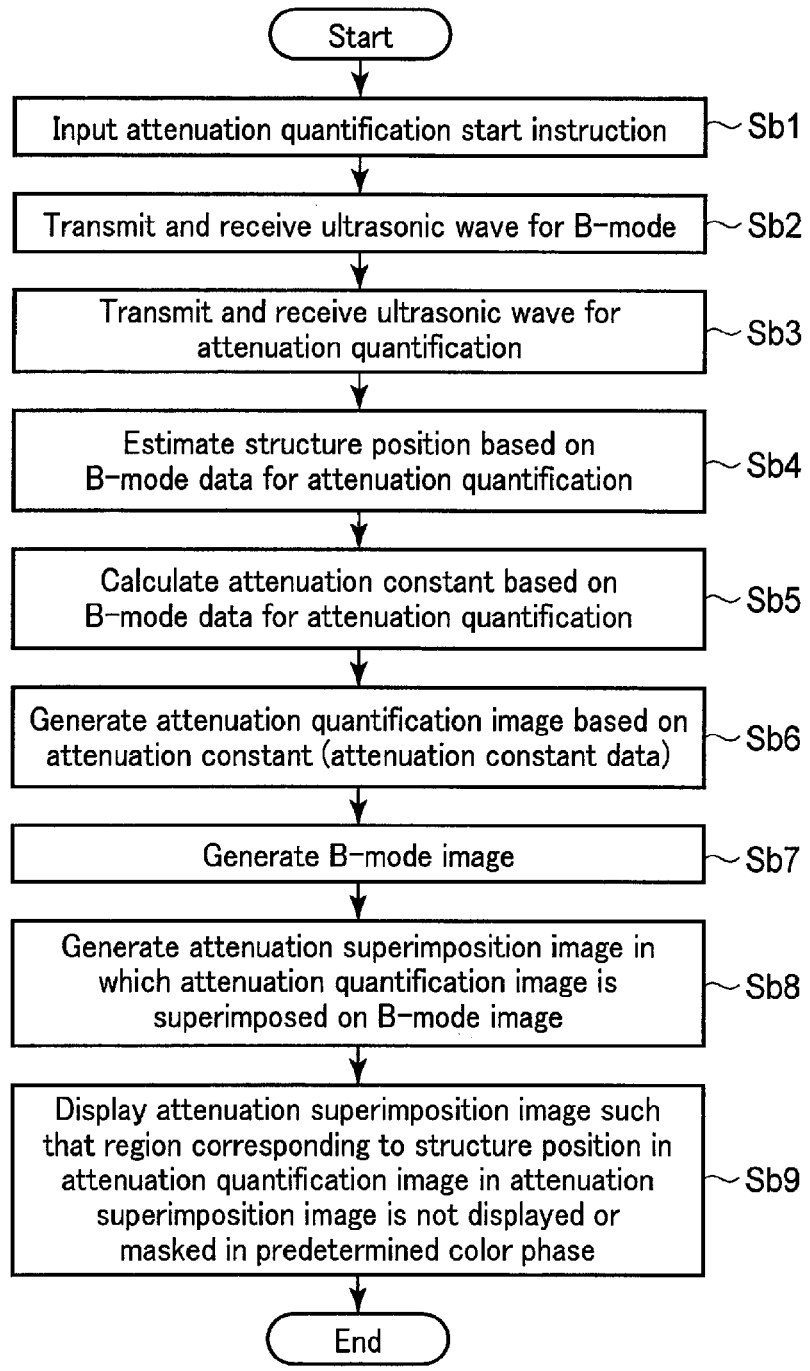
FIG. 6 is a flowchart showing an example of a processing procedure concerning the structure estimation function and the tissue characterization analysis function according to a variation of the present embodiment.

Hereinafter, a processing procedure concerning the structure estimation function and the tissue characterization analysis function according to this variation will be described. FIG. 6 is a flowchart showing an example of a processing procedure concerning the structure estimation function and the tissue characterization analysis function according to this variation. Since processing from Step Sb1 to Step Sb4 and Step Sb7 is similar to the processing in Step Sa1 to Step Sa4 and Step Sa1 in FIG. 5, the description will be omitted.

An attenuation constant is calculated over a collection region based on B-mode data for attenuation quantification (Step Sb5). By virtue of the processing in Step Sb5, attenuation constant data in a scanned region being substantially the same as a scanned region concerning a B-mode image is generated. An attenuation quantification image is generated based on the attenuation constant data in a collection region (Step Sb6).

An attenuation superimposition image in which the attenuation quantification image having a predetermined opacity or transparency is superimposed on the B-mode image is generated (Step Sb8). The attenuation superimposition image is displayed on the monitor 7 such that a region corresponding to a structure position in the attenuation quantification image in the attenuation superimposition image is not displayed or masked in predetermined color phase (Step Sb9).

According to the above described constitution, the following effects can be obtained.

According to the ultrasonic diagnosis apparatus 1 of the present embodiment and variation, the tissue characterization (such as the attenuation amount such as the attenuation constant, the modulus of elasticity, the viscosity, and the hardness) can be displayed with respect to a non-structure region by determining presence of a structure. Namely, according to the ultrasonic diagnosis apparatus 1, when the tissue characterization is displayed as a color image, a color non-display state is achieved in a region where it is determined that there is a structure, and a B-mode image of the background can be displayed. Alternatively, according to the ultrasonic diagnosis apparatus 1, when the tissue characterization is displayed as a color image, in a region where it is determined that there is a structure, the tissue characterization can be displayed while being masked in predetermined color phase different from the color image.

For example, comparing the attenuation superimposition image in FIG. 4 displayed on the monitor 7 in the present embodiment and variation and an image in FIG. 11 in the prior art, in the image in FIG. 11, as a result of calculation of attenuation constants in the entire region regardless of presence of a structure, portions having various low and high attenuation constant values are displayed. Thus, in the image in FIG. 11, it is difficult to judge how much the attenuation constant of a tissue to which attention of an operator is paid is. On the other hand, in the attenuation superimposition image in FIG. 4 displayed on the monitor 7 in the present embodiment and variation, since the tissue characterization in a region corresponding to a structure position is not displayed, an operator can grasp a degree of attenuation showing the tissue characterization at first glance.

From the above, according to the ultrasonic diagnosis apparatus 1 of the present embodiment and variation, since reliable analysis results are displayed in a region except for an estimated structure position without allowing an operator to judge whether or not displayed images or numerical values of the analysis results of the tissue characterization are appropriate, the accuracy of obtained analysis results and reproducibility can be enhanced. In addition, according to the ultrasonic diagnosis apparatus 1 of the present embodiment and variation, in displayed images of the analysis results, since an operator is not required to judge whether or not the displayed images are appropriate, a temporal or mental burden for the operator can be reduced, and diagnosis accuracy can be enhanced.

(First Application)

The present embodiment and the present variation differ in that reliability of a representative value of an attenuation constant in ROI (hereinafter referred to as measurement ROI) set in an attenuation superimposition image displayed on the monitor 7 is determined, and the representative value is calculated and displayed according to the determination result. The measurement ROI is a region concerning calculation of the representative value in the measurement ROI and determination of reliability for the representative value.

A setting function 291 has a function of setting the measurement ROI on an attenuation superimposition image displayed on the monitor 7. When an attenuation quantification image is displayed on the monitor 7, the setting function 291 may set the measurement ROI on the attenuation quantification image. When a B-mode image is displayed on the monitor 7, the setting function 291 may set the measurement ROI on the B-mode image.

An analysis function 299 has a function of calculating reliability for representative values representing a plurality of attenuation constants included in the measurement ROI, a function of comparing the reliability and a reliability determination threshold and thereby determining the reliability for a representative value, and a function of calculating a representative value concerning the measurement ROI when the reliability is larger than the reliability determination threshold.

A display function has a function of displaying the measurement ROI on an attenuation superimposition image on the monitor in response to input of an instruction of starting measurement (hereinafter referred to as a measurement start instruction) via the input apparatus 5 and a function of displaying a representative value or predetermined notification on the monitor 7 in response to the determination result obtained by the analysis function 299.

The storage circuitry 25 stores programs concerning various functions according to this application. The storage circuitry 25 stores reliability determination thresholds and predetermined notifications. The reliability determination threshold is a threshold for determination of the reliability of the representative value calculated by the analysis function 299. The predetermined notification is a character string or the like for notifying an operator or the like via the monitor 7 of the fact that for example when the reliability is less than the reliability determination threshold, the representative value has no reliability, is not suitable, and cannot be measured.

The input apparatus 5 inputs the measurement start instruction by an instruction from an operator. The input apparatus 5 inputs an instruction of determining a position of the measurement ROI on an attenuation superimposition image displayed on the monitor 7 in accordance with operator's operation via an interface such as a trackball or a panel button.

The processing circuitry 29 achieving the display function displays the measurement ROI on the attenuation superimposition image displayed on the monitor 7 in response to the measurement start instruction from an operator via the input apparatus 5. The processing circuitry 29 achieving the setting function 291 sets the measurement ROI on an attenuation superimposition image in response to a determination instruction from an operator via the input apparatus 5.

The processing circuitry 29 achieving the analysis function 299 calculates the reliability for representative values representing a plurality of attenuation constants included in the measurement ROI, based on a pixel value included in the measurement ROI. Examples of the representative values include a mean value, median, and mode of a plurality of attenuation constants included in the measurement ROI on an attenuation quantification image.

Specifically, the processing circuitry 29 determines as an area of the measurement ROI the number of pixels included in the measurement ROI (the number will be hereinafter referred to as a measurement pixel number). The processing circuitry 29 compares a plurality of variance ratios and a structure determination threshold included in the measurement ROI and determines, as an area of a structure in the measurement ROI, the number of pixels corresponding to the variance ratio larger than the structure determination threshold. The processing circuitry 29 calculates a ratio of the area of the structure to the area of the measurement ROI (the ratio will be hereinafter referred to as a structure area ratio). At this time, the reliability is, for example, a difference value obtained by subtracting an area ratio from 1.

The processing circuitry 29 may calculate a ratio of an area of a non-structure region to the area of the measurement ROI (the ratio will be hereinafter referred to as a non-structure area ratio). In this time, the reliability corresponds to the non-structure area ratio. Specifically, the processing circuitry 29 compares a plurality of variance ratios and the structure determination threshold included in the measurement ROI and determines, as a non-structure area in the measurement ROI, the number of pixels corresponding to the variance ratio smaller than the structure determination threshold.

The reliability is not limited to the fact that it is based on the structure area ratio or the non-structure area ratio calculated using the variance ratio. Namely, the reliability may be a ratio of the number of pixels having color phase showing an attenuation constant to the measurement pixel number. The reliability may be the variance ratio calculated by the formula (2).

The reliability may be calculated such that the number of pixels concerning a luminance value higher than a predetermined luminance value in a region included in the measurement ROI on a B-mode image with respect to the measurement pixel number is taken to be the structure area ratio. In this case, the predetermined luminance value is stored in the storage circuitry 25. The predetermined luminance value is, for example, a luminance value representing a structure such as the blood vessel wall.

The reliability may be calculated such that the number of pixels concerning a luminance value lower than the predetermined luminance value in the region included in the measurement ROI on the B-mode image with respect to the measurement pixel number is taken to be the non-structure area ratio. When the reliability is calculated using B-mode data, the processing circuitry 29 allows a gain reverse correction function 295, a sound field characteristic correction function 297, and the analysis function 299 to generate attenuation constant data with the use of the B-mode data used in calculation of the reliability.

The processing circuitry 29 compares the reliability and the reliability determination threshold and thereby determines the reliability for the representative value concerning the measurement ROI. Specifically, the processing circuitry 29 determines that measurement of a representative value in the measurement ROI is appropriate when the reliability is larger than the reliability determination threshold. The processing circuitry 29 determines that measurement of the representative value in the measurement ROI is not appropriate when the reliability is not more than the reliability determination threshold.

When it is determined that measurement of the representative value in the measurement ROI is appropriate, the processing circuitry 29 calculates a representative value of the attenuation amount in the measurement ROI based on the attenuation amount at each of a plurality of positions in the measurement ROI. Specifically, the processing circuitry 29 calculates representative values such as a mean value, median, and mode of attenuation constants, based on the attenuation constants included in the measurement ROI. The processing circuitry 29 may calculate the representative values with the use of a differential value (hereinafter referred to as a mean differential value) obtained by differentiating a mean value of the measurement ROI in attenuation data along the depth direction. At this time, the following calculation procedure is performed, for example.

First, the processing circuitry 29 averages a plurality of pixel values along a plurality of scanning lines (hereinafter referred to as a measurement scanning line) included in the measurement ROI in the attenuation data and thereby generates a measurement mean value. Then, the processing circuitry 29 averages a plurality of pixel values along a measurement scanning line between an abutment surface in which an ultrasonic probe 3 is abutted against a body surface of a subject P and the measurement ROI and thereby generates an ROI upper mean value. The processing circuitry 29 divides a value, obtained by differentiating the measurement mean value from the ROI upper mean value, by a thickness of the measurement ROI along a center line of the measurement scanning line. The value according to this division corresponds to the above-described mean differential value. Finally, the processing circuitry 29 divides a value, obtained by multiplying the mean differential value by ½ while considering two ways of ultrasonic waves, by the transmission center frequency of an ultrasonic wave for attenuation quantification and thereby calculates a representative value.

The processing circuitry 29 averages a plurality of pixel values along a measurement scanning line in a region deeper than the measurement ROI and thereby may generate an ROI lower mean value. In this case, the processing circuitry 29 divides a value, obtained by differentiating the ROI lower mean value from the measurement mean value, by the thickness of the measurement ROI along the center line of the measurement scanning line. The value according to this division corresponds to the above-described mean differential value.

The processing circuitry 29 controls the image compositing circuitry 23 or the monitor 7 such that a representative value is displayed in a measurement result display region in the monitor 7. In an image display region in the monitor 7, the measurement result display region is different from a display region of an attenuation superimposition image on which the measurement ROI is superimposed. The monitor 7 displays a representative value and the name of the measurement ROI in the measurement result display region in addition to display of the attenuation superimposition image on which the measurement ROI is superimposed.

When it is determined that measurement of the representative value in the measurement ROI is not appropriate, the processing circuitry 29 controls the image compositing circuitry 23 or the monitor 7 such that a predetermined notification is displayed in the measurement result display region. The monitor 7 displays a predetermined notification and the name of the measurement ROI in the measurement result display region in addition to display of the attenuation superimposition image on which the measurement ROI is superimposed.

Figure 7:
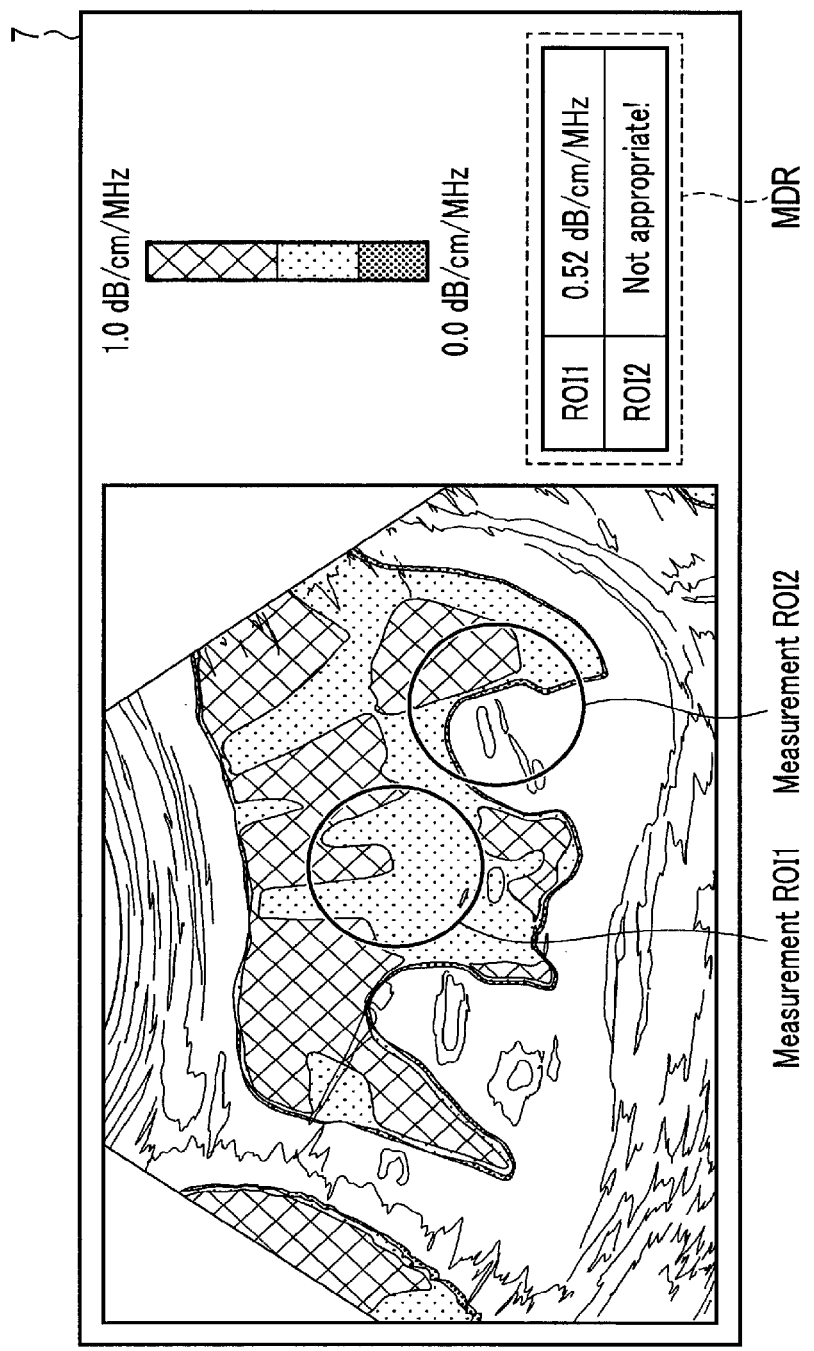
FIG. 7 is a view showing a first application of the present embodiment and showing an example in which when it is determined that measurement of a representative value in measurement ROI1 is appropriate and measurement of a representative value in measurement ROI2 is not appropriate, a representative value or a predetermined notification corresponding to the name of measurement ROI and an attenuation superimposition image on which the measurement ROI is superimposed are displayed on the monitor.

FIG. 7 is a view showing an example in which when it is determined that measurement of a representative value in measurement ROI1 is appropriate and measurement of a representative value in measurement ROI2 is not appropriate, a representative value and a predetermined notification corresponding to the name of the measurement ROI and an attenuation superimposition image on which the measurement ROI is superimposed are displayed on the monitor 7.

As shown in FIG. 7, the measurement ROI1 is set on a region including the uniform parenchyma of the liver, and an attenuation quantification image is displayed in the measurement ROI1. In such a case, since there are few structures in the measurement ROI1, the attenuation constant can be calculated with high accuracy in the measurement ROI1. Thus, as shown in FIG. 7, the names of the measurements ROI and a calculated representative value are displayed in a measurement result display region MDR.

On the other hand, as shown in FIG. 7, the measurement ROI2 is set in a region including a vessel region, and an attenuation quantification image is not displayed in a majority of regions in the measurement ROI2. In such a case, since the attenuation constant cannot be calculated with high accuracy in the measurement 8012, a representative value is not calculated. Thus, as shown in FIG. 7, the names of the measurements ROI and a predetermined notification "Not appropriate!" are displayed in the measurement result display region MDR.

(Representative Value Calculation Function)

The representative value calculation function is a function of determining the reliability of a representative value of an attenuation constant in the measurement ROI and calculating and displaying the representative value in accordance with the determination result. The representative value calculation function has a function of comprehensively achieving the above-described setting function 291, analysis function 299, and display function. The processing circuitry 29 (processor) achieving the representative value calculation function may function as a representative value calculation unit.

Figure 8:
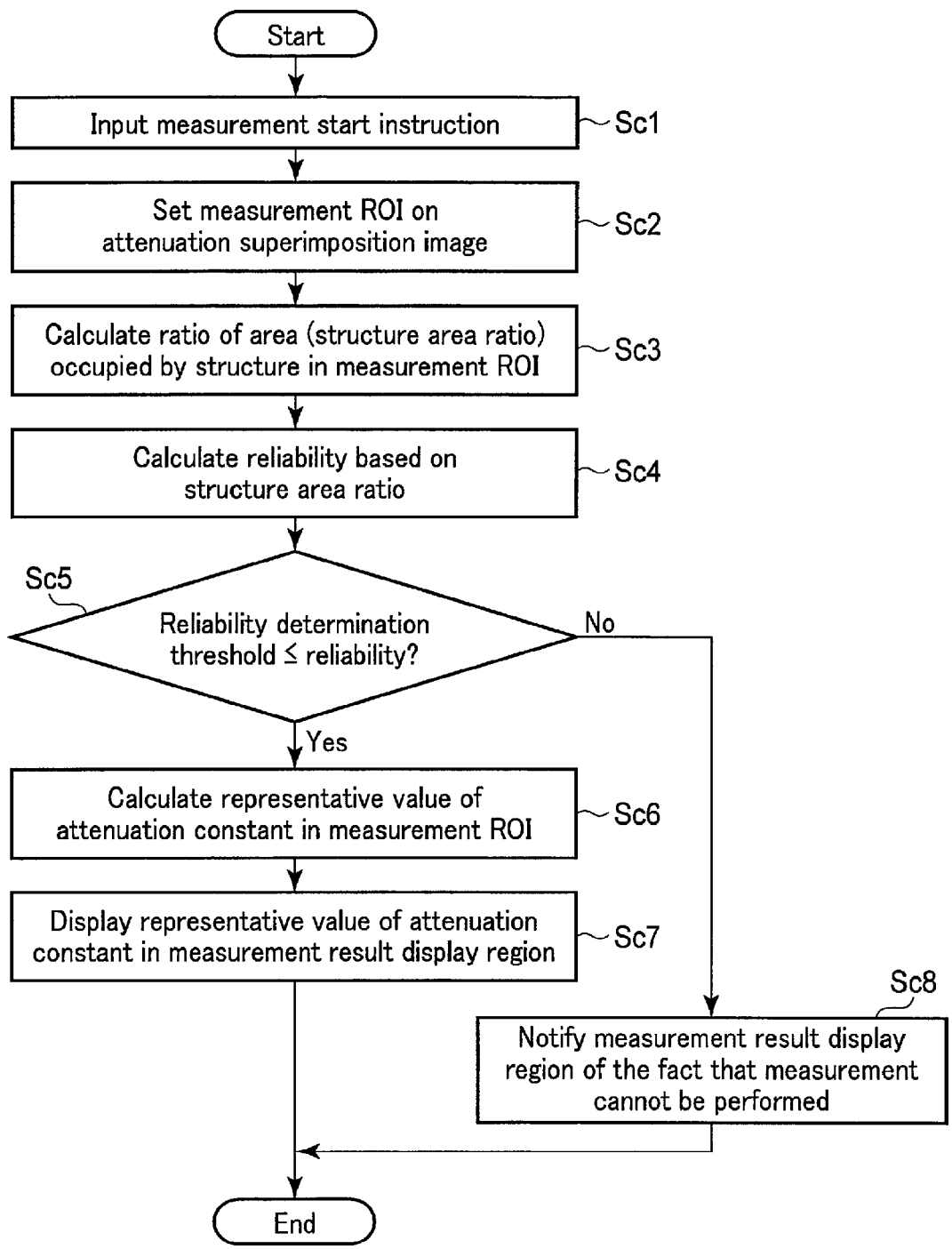
FIG. 8 is a flowchart showing an example of a processing procedure concerning a representative value calculation function according to the first application of the present embodiment.

FIG. 8 is a flowchart showing an example of a processing procedure concerning the representative value calculation function according to the present application. The flowchart shown in FIG. 8 is a processing procedure executed as a continuation of the flowchart in FIG. 5 or the flowchart in FIG. 6.

The measurement start instruction is input by the input apparatus 5 (Step Sc1). The measurement ROI is displayed on an attenuation superimposition image displayed on the monitor 7 in response to the input of the measurement start instruction. The measurement ROI is set on the attenuation superimposition image in response to input of the determination instruction (Step Sc2). A ratio of an area occupied by a structure in the set measurement ROI (structure area ratio) is calculated (Step Sc3). The reliability is determined based on the structure area ratio (Step Sc4).

If the reliability is more than the reliability determination threshold (Step Sc5), the representative value of the attenuation constant in the measurement ROI is calculated (Step Sc6). Then, the representative value is displayed in the measurement result display region (Step Sc7). If the reliability is less than the reliability determination threshold (Step Sc5), a notification showing that measurement cannot be performed is displayed in the measurement result display region (Step Sc8). The processing from Step Sc3 to Step Sc8 is repeated for each setting of the measurement ROI. When a plurality of the measurements ROI are set on the attenuation superimposition image, the processing from Step Sc3 to Step Sc8 is repeated with respect to each of the measurements ROI.

According to the above described constitution, the following effects can be obtained in addition to the effects according to the present embodiment and variation.

According to the ultrasonic diagnosis apparatus 1 of the present application, when a representative value of the attenuation amount in the measurement ROI designated by an operator is displayed, when there are many structures included in the measurement ROI and when the structure included in the measurement ROI is large, that is, when the degree of reliability showing the reliability of a representative value of numerical values showing the tissue characterization in the measurement ROI is lower than the reliability determination threshold, the notification showing that measurement cannot be performed can be displayed without displaying the representative value. Namely, according to the ultrasonic diagnosis apparatus 1 of the present application, when there are many structures included in the measurement ROI or when the structure included in the measurement ROI is large, a representative value of an attenuation constant in the measurement ROI is not displayed, regarding that the representative value is not reliable, and an operator can be prompted to set the measurement ROI again.

From the above, according to the ultrasonic diagnosis apparatus 1 of the present application, since reliable quantification results (representative values such as an attenuation constant showing the tissue characterization) are displayed, an operator is not required to judge whether or not a displayed representative value is appropriate, a temporal or mental burden for the operator is reduced, and, in addition, reproducibility and accuracy of measurement of the tissue characterization can be enhanced.

(Second Application)

The second application differs from the first application in that a representative value corresponding to the measurement ROI is calculated regardless of the reliability according to the presence of a structure in the measurement ROI, the area of the structure, or the like, and the reliability and representative value corresponding to the measurement ROI are displayed.

The storage circuitry 25 stores at least one threshold (hereinafter referred to as a rank threshold) configured to rank the reliability. The number of rank thresholds is smaller by 1 than the number of ranks. The storage circuitry 25 stores a program concerning the ranking of the reliability (the program will be hereinafter referred to as a ranking program). When the reliability itself is displayed, the rank threshold and the ranking program are not required.

The processing circuitry 29 achieving an analysis function 299 calculates a representative value regardless of the reliability. The processing circuitry 29 calculates the reliability corresponding to the measurement ROI. The processing circuitry 29 reads out the rank threshold and the ranking program from the storage circuitry 25. The processing circuitry 29 compares the reliability and the rank threshold in accordance with the ranking program and thereby ranks the reliability. Hereinafter, for ease of explanation, it is assumed that there are two rank thresholds (hereinafter referred to as a high rank threshold and a low rank threshold). In this case, there are three ranks (for example, A, B, and C ranks). The number of the rank thresholds is not limited to two. Namely, the number of the ranks is not limited to three and may be arbitrarily set.

When the reliability is more than the high rank threshold, the processing circuitry 29 determines the rank of the reliability concerning the measurement ROI as "A". When the reliability is not more than the high rank threshold and is more than the low rank threshold, the processing circuitry 29 determines the rank of the reliability concerning the measurement ROI as "B". When the reliability is not more than the low rank threshold, the processing circuitry 29 determines the rank of the reliability concerning the measurement ROI as "C". The processing circuitry 29 makes the determined rank correspond to the measurement ROI related to the reliability and allows the storage circuitry 25 to store the rank. The processing circuitry 29 controls the image compositing circuitry 23 or a monitor 7 such that a representative value and a rank are displayed in a measurement result display region in the monitor 7.

The monitor 7 displays a representative value, a rank, and the name of the measurement ROI in the measurement result display region in addition to display of an attenuation superimposition image on which the measurement ROI is superimposed. The monitor 7 may display the reliability itself in the measurement result display region together with the representative value and the name of the measurement ROI. In this case, the monitor 7 displays, as the reliability, the variance ratio calculated by the formula (2) or a non-structure area ratio, a differential value obtained by differentiating a structure area ratio from 1, and the like.

FIG. 9 is a view showing an example in which representative values and the ranks of reliability corresponding to the names of the measurements ROI and an attenuation superimposition image on which the measurements ROI are superimposed are displayed on the monitor 7. FIG. 9 shows an example in which the reliability is displayed in three stages A, B, and C. As shown in FIG. 9, the measurement ROI1 is set on a region including the uniform parenchyma of the liver, and an attenuation quantification image is displayed in the measurement ROI1. In such a case, since there are few structures in the measurement ROI1, the rank of the reliability is determined as "A" and displayed in a measurement result display region MDR together with a representative value concerning the measurement ROI1.

As shown in FIG. 9, measurement ROI2 is set in a region including a vessel region, and an attenuation quantification image is not displayed in a majority of regions in the measurement ROI2. In such a case, since structures exist in a majority of regions in the measurement ROI2, the rank of the reliability is determined as "C" and displayed in the measurement result display region MDR together with a representative value concerning the measurement ROI2.

(Reliability Display Function)

The reliability display function is a function of displaying the reliability or the rank of the reliability in the measurement result display region MDR together with a representative value calculated regardless of the reliability according to the presence of a structure in the measurement ROI, the area of the structure, or the like. The reliability display function has a function of comprehensively achieving the setting function 291, the analysis function 299, and the display function in the first application.

Figure 10:
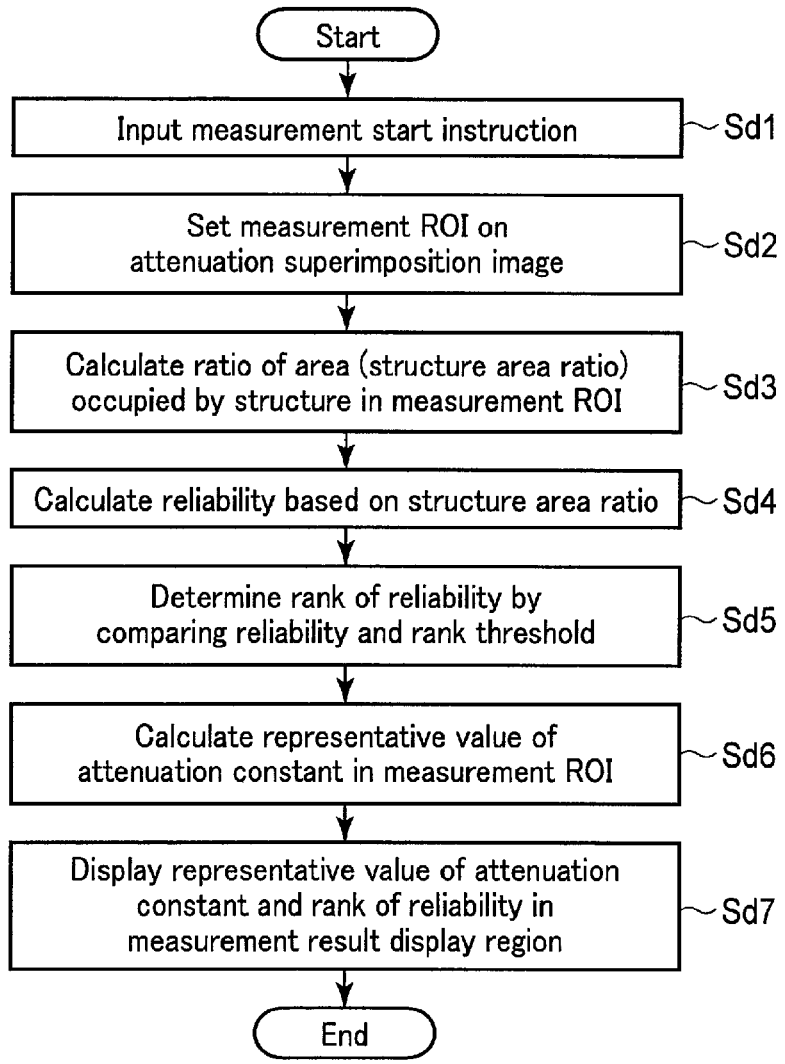
FIG. 10 is a flowchart showing an example of a processing procedure according to the second application of the present embodiment concerning a reliability display function.

FIG. 10 is a flowchart showing an example of a processing procedure concerning the reliability display function according to the present application. The flowchart shown in FIG. 10 is a processing procedure executed as a continuation of the flowchart in FIG. 5 or the flowchart in FIG. 6. Since processing from Step Sd1 to Step Sd4 and Step Sd6 is similar to the processing in Step Sc1 to Step Sc4 and Step Sc6 in FIG. 8, the description will be omitted.

After the processing in Step Sd4, the reliability and the rank threshold are compared, whereby the rank of the reliability is determined (Step Sd5). When the reliability itself is displayed with a representative value, the processing in Step Sd5 is not required.

After the processing in Step Sd6, a representative value of an attenuation constant and the rank of the reliability are displayed in the measurement result display region together with the name of the measurement ROI (Step Sd7). The processing from Step Sd3 to Step Sd7 is repeated for each setting of the measurement ROI. When a plurality of the measurements ROI are set on an attenuation superimposition image, the processing from Step Sd3 to Step Sd6 is repeated with respect to each of the measurements ROI, and representative values and ranks corresponding to the respective measurements ROI are listed in the measurement result display region.

According to the above described constitution, the following effects can be obtained in addition to the effects according to the present embodiment and variation.

According to the ultrasonic diagnosis apparatus 1 of the present application, when a representative value of the attenuation amount included in the measurement ROI is displayed, the reliability corresponding to the size and degree of a structure included in the measurement ROI can be displayed together. Namely, according to the ultrasonic diagnosis apparatus 1 of the present application, even when a place where a reliable result is obtained by the tissue characterization of a target tissue is hardly found in the measurement ROI, certain quantification results (representative values) can be obtained. For example, in cases in which the entire liver is nonuniform, such as a case in which fibrosis has progressed, attenuation quantification results (representative values) can be displayed together with the reliability in any place.

From the above, according to the ultrasonic diagnosis apparatus 1 of the present application, since the level of reliability of a quantification result can be displayed, an operator can refer to the quantification result as reference information at ease and use the quantification result in diagnosis.

(Third Application)

The third application differs from the present embodiment and variation and the first and second applications in that an MRI apparatus is applied as a medical diagnostic apparatus. A calculator in the MRI apparatus (not shown) includes the image generating circuitry 19, the image memory 21, the image compositing circuitry 23, the storage circuitry 25, the interface circuitry 27, the processing circuitry 29, and a sequencer (not shown). The calculator is connected to an input apparatus 5, a monitor 7, and so on.

The processing circuitry 29 in the calculator executes various functions as described above. The storage circuitry 25 in the calculator stores various data such as programs concerning various functions executed by the processing circuitry 29.

The processing circuitry 29 achieving an estimation function 293 in this application estimates a position of a structure in a cross section corresponding to MR (Magnetic Resonance) scanning, based on data obtained by MR scanning (the data will be hereinafter referred to as MR data) utilizing a magnetic resonance phenomenon, as described above.

The processing circuitry 29 achieving an analysis function 299 in this application analyzes the tissue characterization at a plurality of positions in a subject except for a structure position estimated by the estimation function 293 in a cross section, based on data obtained by MR scanning utilizing the nuclear magnetic resonance phenomenon. The tissue characterization in this application is an amount showing characterization of a tissue to be diagnosed, such as the attenuation amount, modulus of elasticity (Young's modulus), viscosity, and distortion. In this application, for example, the tissue characterization is obtained by MR elastography (MRE). At this time, data concerning analysis of the tissue characterization corresponds to MRE data obtained by MRE scanning.

Hereinafter, for ease of explanation, MRE is taken to be an elastography method of observing a wave propagating inside a subject P with the use of a phase image in which an image of a phase of a proton is created, based on vibration due to a nonmagnetic vibration mechanism provided outside the subject P.

The image generating circuitry 19 in the calculator generates an MR image based on MR data obtained by MR scanning executed with respect to the subject P under control by the sequencer. Further, the image generating circuit 19 generates an MRE image based on MRE data obtained by MRE scanning executed with respect to the subject P under control by the sequencer. The MR image or the MRE image is used in a setting function 291 and the estimation function 293. The MRE image is further used in the analysis function 299.

In this application, in an attenuation superimposition image displayed on the monitor 7, the background image in FIG. 4 is the MR image, and an attenuation quantification image corresponds to the MRE image. Since a processing procedure concerning a structure estimation function and a tissue characterization analysis function according to this application is substantially similar to FIG. 5, different processing will be described. The MR image and the MRE image may not be displayed to be superimposed but may be individually displayed.

In this application, the processing corresponding to Step Sa2 in FIG. 5 is processing for executing MR scanning with respect to the subject P in accordance with an imaging sequence for collecting MR data. In this application, the processing corresponding to Step Sa3 in FIG. 5 is processing for executing MRE scanning with respect to a subject in accordance with an imaging sequence for collecting MRE data.

In this application, the processing corresponding to Step Sa4 in FIG. 5 is processing for estimating a position of a structure based on the MRE data. In this application, the processing corresponding to Step Say in FIG. 5 is processing for calculating an attenuation constant based on the MRE data at a plurality of positions except for a position of a structure.

In this application, the processing corresponding to Step Sa1 in FIG. 5 is processing for generating an MR image. In this application, the processing corresponding to Step Sa8 in FIG. 5 is processing for performing display while superimposing an attenuation quantification image on an MR image.

According to the MRI apparatus of this application, it can be similarly executed in the variation of the present embodiment, the first application, and the second application.

According to the above-described constitution, the following effects can be obtained as in the present embodiment and variation.

According to the MRI apparatus of this application, the tissue characterization can be displayed with respect to a non-structure region by determining the presence of a structure. Namely, according to the MRI apparatus, when the tissue characterization is displayed as a color image, a color non-display state is achieved in a region where it is determined that there is a structure, and an MR image of the background can be displayed. Alternatively, according to the MRI apparatus, when the tissue characterization is displayed as a color image, in a region where it is determined that there is a structure, the tissue characterization can be displayed while being masked in predetermined color phase different from the color image.

From the above, according to the MRI apparatus of this application, since reliable analysis results are displayed in a region except for an estimated structure position without allowing an operator to judge whether or not displayed images or numerical values of the analysis results of the tissue characterization are appropriate, the accuracy of obtained analysis results and reproducibility can be enhanced. In addition, according to MRI of this application, in displayed images of the analysis results, since an operator is not required to judge whether or not the displayed images are appropriate, a temporal or mental burden for the operator can be reduced, and diagnosis accuracy can be enhanced.

In addition, each function associated with each embodiment can also be implemented by installing programs for executing the corresponding processing in a computer such as a workstation and mapping them in a memory. In this case, the programs which can cause the computer to execute the corresponding techniques can be distributed by being stored in recording media such as magnetic disks (hard disks and the like), optical disks (CD-ROMs, DVDs, and the like), and semiconductor memories.

According to the above-described medical diagnostic apparatus and medical analysis method, the tissue characterization in the subject P is analyzed, and the tissue characterization in a non-structure region in the subject can be displayed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical diagnostic apparatus comprising:
processing circuitry configured to estimate a position of a structure in a subject based on data obtained by scanning with respect to the subject and to analyze tissue characterization corresponding to attenuation of an ultrasonic wave propagating in the subject based on the data used for estimating the position of the structure; and
display circuitry configured to display an analysis result of the tissue characterization obtained by the processing circuitry with respect to a plurality of positions in the subject except for the estimated position of the structure.

2. The medical diagnostic apparatus according to claim 1, wherein the processing circuitry is configured
to estimate the structure position based on the data obtained by ultrasonic scanning with respect to the subject, and
to analyze the tissue characterization at the positions based on the data obtained by the ultrasonic scanning with respect to the subject.

3. The medical diagnostic apparatus according to claim 2, wherein the processing circuitry is configured
to set a plurality of regions in a scanning region in the ultrasonic scanning,
to calculate a variance value and a mean value based on the data in each of the regions, and
to estimate the structure position in the scanning region based on the variance value and the mean value.

4. The medical diagnostic apparatus according to claim 2, wherein the processing circuitry is configured
to estimate the structure position in the scanning region by executing contrast false alarm rate processing with respect to a scanning region in the ultrasonic scanning.

5. The medical diagnostic apparatus according to claim 2, wherein the processing circuitry is configured to calculate, as the tissue characterization, a feature quantity concerning an attenuation amount of the ultrasonic wave propagating in the subject, and
the display circuitry is configured to display the attenuation amount as the analysis result at each of a plurality of positions in the subject except for the structure position.

6. The medical diagnostic apparatus according to claim 5, further comprising input interface circuitry configured to input a region of interest to an ultrasonic image corresponding to the ultrasonic scanning,
wherein the processing circuitry is configured to calculate a representative value representing the attenuation amount in the region of interest, based on the attenuation amount at each of a plurality of positions in the region of interest, and
the display circuitry is configured to display the representative value with the region of interest.

7. The medical diagnostic apparatus according to claim 6, wherein the processing circuitry is configured to calculate a degree of reliability concerning the representative value based on a pixel value in the region of interest, and
the display circuitry is configured to display the reliability with the representative value.

8. The medical diagnostic apparatus according to claim 5, wherein the processing circuitry is configured
to cancel gain correction with respect to the data,
to cancel dependency of sound field characteristics in the data based on the sound field characteristics in the ultrasonic scanning, and
to calculate the attenuation amount as the tissue characterization based on correction data in which the gain correction and the dependency of the sound field characteristics are cancelled in the data.

9. The medical diagnostic apparatus according to claim 5, further comprising ultrasonic transmitting circuitry configured to transmit a plurality of ultrasonic waves having different frequencies to the subject in the ultrasonic scanning,
wherein the processing circuitry is configured to calculate, as the tissue characterization, a difference between the attenuation amounts due to the difference in frequency with the use of the data corresponding to each of the ultrasonic waves.

10. The medical diagnostic apparatus according to claim 5, further comprising ultrasonic transmitting circuitry configured to transmit an ultrasonic wave in a band narrower than a frequency band in ultrasonic transmission concerning a B-mode in the ultrasonic scanning, wherein the processing circuitry is configured
- to execute frequency analysis with respect to data obtained by reception of the ultrasonic wave in the narrow band, and
- to calculate the attenuation amount based on frequency characteristics in the frequency analysis.

11. The medical diagnostic apparatus according to claim 5, wherein the display circuitry is configured to perform display such that the attenuation amount is superimposed on a B-mode image in color phase corresponding to a value of the attenuation amount at a predetermined opacity or transparency.

12. The medical diagnostic apparatus according to claim 1, wherein the processing circuitry is configured to calculate at least one of viscosity of a tissue in the subject and elasticity of the tissue.

13. The medical diagnostic apparatus according to claim 1, wherein the processing circuitry is configured
- to estimate the structure position based on data obtained by scanning using a nuclear magnetic resonance phenomenon as the scanning, and
- to analyze the tissue characterization at the positions based on the data obtained by the scanning using the nuclear magnetic resonance phenomenon.

14. The medical diagnostic apparatus according to claim 1, wherein the processing circuitry is configured to generate a B-mode image based on the data, and the display circuitry is configured to display the analysis result on the B-mode image.

15. A medical diagnostic apparatus comprising:
processing circuitry configured
- to estimate a position of a structure in a subject based on data obtained by scanning with respect to the subject, and
- to analyze tissue characterization corresponding to elasticity or viscosity of a tissue in the subject based on the data used for estimating the position of the structure, wherein the tissue characterization is obtained from propagation velocity of a shear wave generated in the subject, and display circuitry configured to display an analysis result of the tissue characterization obtained by the processing circuitry with respect to a plurality of positions in the subject except for the estimated position of the structure.

16. A medical analysis method comprising:
estimating a position of a structure in a subject based on data obtained by scanning with respect to the subject;
analyzing tissue characterization corresponding to elasticity or viscosity of a tissue in the subject based on the data used for estimating the position of the structure, wherein the tissue characterization is obtained from propagation velocity of a shear wave generated in the subject; and
displaying, on a monitor, an analysis result of the analyzed tissue characterization with respect to a plurality of positions in the subject except for the estimated position of the structure.

* * * * *